US008124588B2

(12) United States Patent
Seeger et al.

(10) Patent No.: US 8,124,588 B2
(45) Date of Patent: Feb. 28, 2012

(54) CHIMERIC PLASMINOGEN ACTIVATORS AND THEIR PHARMACEUTICAL USE

(75) Inventors: Werner Seeger, Giessen (DE); Andreas Günther, Giessen (DE); Clemens Ruppert, Giessen (DE); Philipp Markart, Giessen (DE); Viktor Magdolen, Munich (DE); Timothy E. Weaver, Morrow, OH (US)

(73) Assignee: Justus Liebig Universität Giessen, Giessen (DE)

( * ) Notice: Subject to any disclaimer, the term of this patent is extended or adjusted under 35 U.S.C. 154(b) by 1262 days.

(21) Appl. No.: 10/583,785

(22) PCT Filed: Dec. 18, 2003

(86) PCT No.: PCT/EP03/14542
§ 371 (c)(1),
(2), (4) Date: Mar. 14, 2007

(87) PCT Pub. No.: WO2005/059142
PCT Pub. Date: Jun. 30, 2005

(65) Prior Publication Data
US 2009/0305961 A1    Dec. 10, 2009

(51) Int. Cl.
*A61K 38/17*    (2006.01)
*C07K 14/435*    (2006.01)
*C07H 21/04*    (2006.01)
*C12N 15/63*    (2006.01)

(52) U.S. Cl. ............ 514/14.6; 514/2; 514/12; 536/23.5; 435/325; 435/320.1; 435/69.1; 435/69.7

(58) Field of Classification Search .................. 530/350; 514/2, 12, 14.6; 536/23.5; 435/325, 69.1, 435/320.1, 69.7
See application file for complete search history.

(56) References Cited

U.S. PATENT DOCUMENTS

| | | | |
|---|---|---|---|
| 4,752,581 | A | 6/1988 | Robinson et al. |
| 4,880,776 | A | 11/1989 | Robinson et al. |
| 4,999,194 | A | 3/1991 | Broeze et al. |
| 5,006,343 | A | 4/1991 | Benson et al. |
| 5,112,755 | A | 5/1992 | Heyneker et al. |
| 5,242,819 | A | 9/1993 | Rajput et al. |
| 5,302,581 | A | 4/1994 | Sarin et al. |
| 5,993,809 | A | 11/1999 | Weaver et al. |
| 6,031,075 | A | 2/2000 | Weaver |

FOREIGN PATENT DOCUMENTS

| | | |
|---|---|---|
| WO | 00/29588 | 5/2000 |
| WO | WO 00/76535 | 12/2000 |

OTHER PUBLICATIONS

Haagsman, Henk P. and Robert V. Diemel, Comparitive Biochemistry and Physiology, Part A, 129 (2001) 91-108.

Ruppert, Clemens et al., Thrombosis and Haemostasis, Jan. 2003, V89, p. 53-64.
Idell S., "Endothelium and disordered fibrin turnover in the injured lung: Newly recognized pathways." Crit. Care Med. (2002) vol. 30, pp. 274-280.
Bertozzi, P. et al., "Depressed bronchoalveolar urokinase activity in patients with adult respiratory distress syndrome." N. Engl. J. Med., (1990) vol. 30, pp. 890-897.
Campell, E.J. et al., "Extracellular matrix injury during lung inflammation." Chest, (1987) vol. 92, pp. 161-167.
Burkhardt, A., "Alveolitis and collapse in the pathogenesis of pulmonary fibrosis." Am. Rev. Respir. Dis. (1989) vol. 140, pp. 513-524.
Creuwels, L.A.J.M. et al., "The pulmonary surfactant system: Biochemical and clinical aspects." Lung (1997) vol. 175, pp. 1-39.
Haggsmann, H.P. et al., "Surfactant-associated proteins: functions and structural variation." Comp. Biochem. Physiol. A: Mol. Integr. Physiol. (2001) vol. 129, pp. 91-108.
Crouch, E. et al., "Surfactant proteins A and D and pulmonary host defence." Annu. Rev. Physiol. (2001), vol. 63, pp. 521-554.
Weaver, T.E. et al., "Functions of surfactant proteins B and C." Annu. Rev. Physiol. (2001) vol. 63, pp. 555-578.
Sisson, T.H. et al., "Treatment of bleomycin-induced pulmonary fibrosis by transfer of urokinase-type plasminogen activator genes." Human Gene Therapy (1999), vol. 10, pp. 2315-2323.
Levin, E.G. et al., "Human hepatoma cell line plasminogen activator." J. Lab. Clin. Med. (1983), vol. 102, pp. 500-508.
Peter, K. et al., "Construction and in vitro testing of a novel Fab-Hirudin-based fusion protein that targets fibrin and inhibits thrombin in a factor Xa-dependent manner." Cardiovasc. Pharmacol., (2003), vol. 42, pp. 237-244.
Kerr, D.E. et al., "Comparison of recombinant and synthetically formed monoclonal antibody-bet-lactamase conguates for anticancer . . . " Bioconjugate Chem. (1999), vol. 10, pp. 1084-1089.
Lindbladh C. et al., "Use of genetically prepared enzyme conjugates in enzyme immunoassay." Trends Biochem Sci. (1993), vol. 18(8), pp. 279-283.
Schermuly, R.T. et al., "Differential impact of ultrasonically nebulized versus tracheal-instilled surfactant on ventilation-perfusion (Va/Q) mismatch in a model of acute lung injury." Am. J. Respir. Crit. Care Med. (2000), vol. 161, pp. 152-159.
Castellino F.J. et al., "Structure and function of the plasminogen/plasmin system." Thromb Haemost (2005), vol. 93, pp. 647-654.
Dobrovolsky A.B. et al., "The fibrinolysis system: Regulation of activity and physiologic functions of its main components." Biochemistry (Moscow) (2002), vol. 67 (1), pp. 99-108.
Collen D.C. et al., "Thrombolytic agents." Thromb Haemost (2005), vol. 93, pp. 627-630.
A. Gunther et al., "Surfactant alteration and replacement in acute respiratory distress syndrome", *Respir. Res.* 2001, 2:353-364.

(Continued)

*Primary Examiner* — Chih-Min Kam
(74) *Attorney, Agent, or Firm* — Michael A. Whittaker; Acuity Law Group, P.C.

(57) ABSTRACT

The present invention relates to recombinant chimeric proteins comprising a surfactant protein precursor N-terminally fused to a plasminogen activator or comprising a mature surfactant protein N-terminally or C-terminally fused to a plasminogen activator. The invention is also directed to the corresponding nucleic acid molecules encoding such fusion proteins as well as to a method for their production. The invention further refers to a pharmaceutical composition comprising such a fusion protein and to pharmacological uses of an inventive fusion protein for the prevention and/or treatment of inflammatory and interstitial lung diseases.

28 Claims, 7 Drawing Sheets

OTHER PUBLICATIONS

Figure 1A:
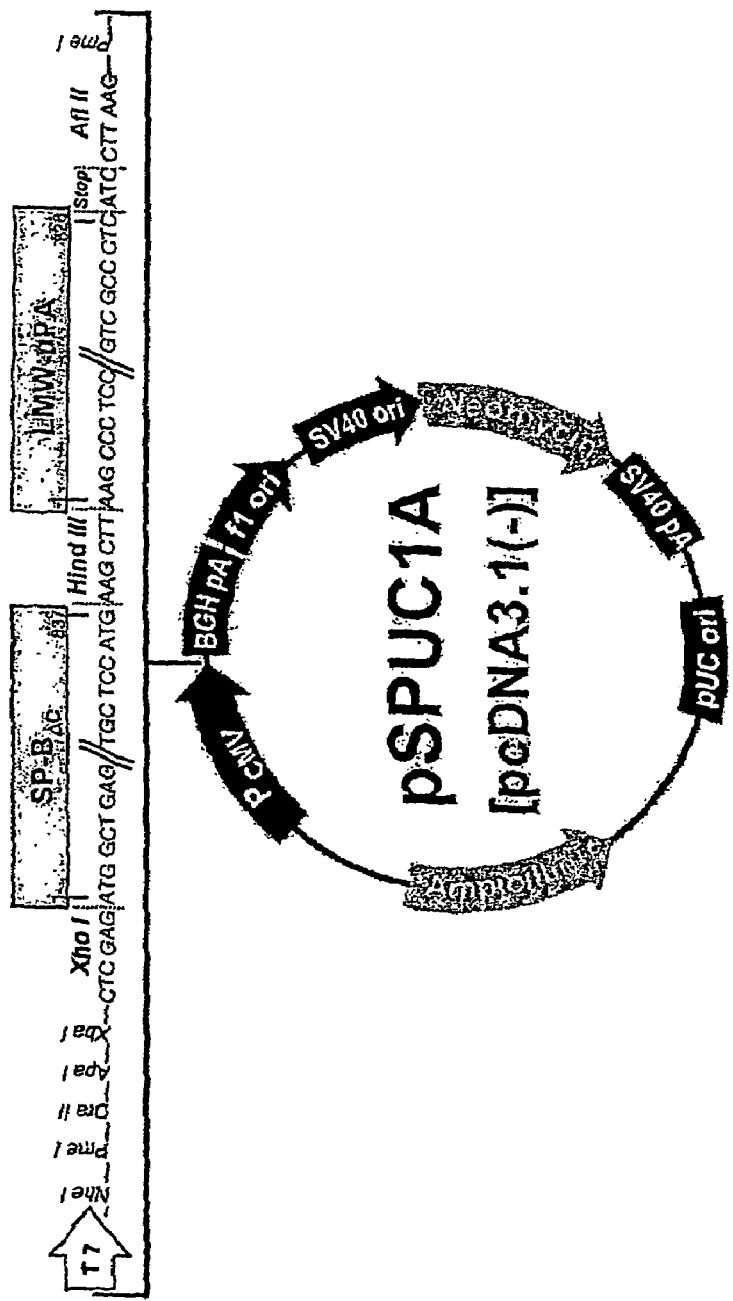

S. Idell et al., "Local Abnormalities in coagulation and Fibrinolytic Pathways Predispose to Alveolar Fibrin Deposition in the Adult Respiratory Distress Syndrome", *J. Clin. Invest.* 1989, 84:695-705.

A. Gunther et al., "Alveolar Fibrin Formation Caused by Enhanced Procoagulant and Depressed Fibrinolytic Capacities in Severe Pneumonia", *Am. J. Respir. Crit. Care Med.* 2000, 161:454-462.

K. Yamada, "Adhesive Recognition Sequences", *J. Biol. Chem.* 1991, 266:12809-12812.

R. Schermuly et al., "Conebulization of surfactant and urokinase restores gas exchange in perfused lungs . . . ", *Am. J. Physiol. Lung Cell. Mol. Physiol.* 2001, 280:L792-L800.

P. Markart et al., "Fibrinolysis-inhibitory capacity of clot-embedded surfactant is enhanced by SP-B and SP-C", *Am. J. Physiol. Lung Cell. Mol. Physiol.* 2003, 284:L69-L76.

A. Gunther et al., "Cleavage of Surfactant-Incorporating Fibrin by Different Fibrinolytic Agents", *Am. J. Respir. Cell Mol. Biol.* 1999, 21:738-745.

C. Ruppert et al., "Chemical Coupling of a Monoclonal Antisurfactant Protein-B Antibody to Human Urokinase for Targeting Surfactant-Incorporating Alveolar Fibrin", *Bioconjugate Chem.* 2002, 13:804-811.

C. Ruppert et al., "Chemical Crosslinking of Urokinase to Pulmonary Surfactant protein B for Targeting Alveolar Fibrin", *Thromb. Haaemost.* 2003, 89:53-64.

Lukovic et al., "Production and characterisation of recombinant forms of human pulmonary surfactant protein C (SP-C): Structure and surface activity" Biochimica et Biophysica Acta 1758 (2006) 509-518.

SEQUENCE LISTING

<160> NUMBER OF SEQ ID NOS: 40

<210> SEQ ID NO 1
<211> LENGTH: 1143
<212> TYPE: DNA
<213> ORGANISM: Homo sapiens
<220> FEATURE:
<221> NAME/KEY: CDS
<222> LOCATION: (1)..(1143)
<223> OTHER INFORMATION: Coding sequence of the surfactant protein B
      precursor

<400> SEQUENCE: 1

```
atg gct gag tca cac ctg ctg cag tgg ctg ctg ctg ctg ccc acg        48
Met Ala Glu Ser His Leu Leu Gln Trp Leu Leu Leu Leu Pro Thr
1               5                   10                  15 ctc tgt ggc cca ggc act gct gcc tgg acc acc tca tcc ttg gcc tgt    96
```

```
Leu Cys Gly Pro Gly Thr Ala Ala Trp Thr Thr Ser Ser Leu Ala Cys
        20                  25                  30 gcc cag ggc cct gag ttc tgg tgc caa agc ctg gag caa gca ttg cag        144
Ala Gln Gly Pro Glu Phe Trp Cys Gln Ser Leu Glu Gln Ala Leu Gln
            35                  40                  45 tgc aga gcc cta ggg cat tgc cta cag gaa gtc tgg gga cat gtg gga        192
Cys Arg Ala Leu Gly His Cys Leu Gln Glu Val Trp Gly His Val Gly
    50                  55                  60 gcc gat gac cta tgc caa gag tgt gag gac atc gtc cac atc ctt aac        240
Ala Asp Asp Leu Cys Gln Glu Cys Glu Asp Ile Val His Ile Leu Asn
65                  70                  75                  80 aag atg gcc aag gag gcc att ttc cag gac acg atg agg aag ttc ctg        288
Lys Met Ala Lys Glu Ala Ile Phe Gln Asp Thr Met Arg Lys Phe Leu
                85                  90                  95 gag cag gag tgc aac gtc ctc ccc ttg aag ctg ctc atg ccc cag tgc        336
Glu Gln Glu Cys Asn Val Leu Pro Leu Lys Leu Leu Met Pro Gln Cys
            100                 105                 110 aac caa gtg ctt gac gac tac ttc ccc ctg gtc atc gac tac ttc cag        384
Asn Gln Val Leu Asp Asp Tyr Phe Pro Leu Val Ile Asp Tyr Phe Gln
        115                 120                 125 aac cag act gac tca aac ggc atc tgt atg cac ctg ggc ctg tgc aaa        432
Asn Gln Thr Asp Ser Asn Gly Ile Cys Met His Leu Gly Leu Cys Lys
130                 135                 140 tcc cgg cag cca gag cca gag cag gag cca ggg atg tca gac ccc ctg        480
Ser Arg Gln Pro Glu Pro Glu Gln Glu Pro Gly Met Ser Asp Pro Leu
145                 150                 155                 160 ccc aaa cct ctg cgg gac cct ctg cca gac cct ctg ctg gac aag ctc        528
Pro Lys Pro Leu Arg Asp Pro Leu Pro Asp Pro Leu Leu Asp Lys Leu
                165                 170                 175 gtc ctc cct gtg ctg ccc ggg gcc ctc cag gcg agg cct ggg cct cac        576
Val Leu Pro Val Leu Pro Gly Ala Leu Gln Ala Arg Pro Gly Pro His
            180                 185                 190 aca cag gat ctc tcc gag cag caa ttc ccc att cct ctc ccc tat tgc        624
Thr Gln Asp Leu Ser Glu Gln Gln Phe Pro Ile Pro Leu Pro Tyr Cys
        195                 200                 205 tgg ctc tgc agg gct ctg atc aag cgg atc caa gcc atg att ccc aag        672
Trp Leu Cys Arg Ala Leu Ile Lys Arg Ile Gln Ala Met Ile Pro Lys
210                 215                 220 ggt gcg cta gct gtg gca gtg gcc cag gtg tgc cgc gtg gta cct ctg        720
Gly Ala Leu Ala Val Ala Val Ala Gln Val Cys Arg Val Val Pro Leu
225                 230                 235                 240 gtg gcg ggc ggc atc tgc cag tgc ctg gct gag cgc tac tcc gtc atc        768
Val Ala Gly Gly Ile Cys Gln Cys Leu Ala Glu Arg Tyr Ser Val Ile
                245                 250                 255 ctg ctc gac acg ctg ctg ggc cgc atg ctg ccc cag ctg gtc tgc cgc        816
Leu Leu Asp Thr Leu Leu Gly Arg Met Leu Pro Gln Leu Val Cys Arg
            260                 265                 270 ctc gtc ctc cgg tgc tcc atg gat gac agc gct ggc cca agg tcg ccg        864
Leu Val Leu Arg Cys Ser Met Asp Asp Ser Ala Gly Pro Arg Ser Pro
        275                 280                 285 aca gga gaa tgg ctg ccg cga gac tct gag tgc cac ctc tgc atg tcc        912
Thr Gly Glu Trp Leu Pro Arg Asp Ser Glu Cys His Leu Cys Met Ser
290                 295                 300 gtg acc acc cag gcc ggg aac agc agc gag cag gcc ata cca cag gca        960
Val Thr Thr Gln Ala Gly Asn Ser Ser Glu Gln Ala Ile Pro Gln Ala
305                 310                 315                 320 atg ctc cag gcc tgt gtt ggc tcc tgg ctg gac agg gaa aag tgc aag        1008
Met Leu Gln Ala Cys Val Gly Ser Trp Leu Asp Arg Glu Lys Cys Lys
                325                 330                 335 caa ttt gtg gag cag cac acg ccc cag ctg ctg acc ctg gtg ccc agg        1056
```

```
Gln Phe Val Glu Gln His Thr Pro Gln Leu Leu Thr Leu Val Pro Arg
            340                 345                 350 ggc tgg gat gcc cac acc acc tgc cag gcc ctc ggg gtg tgt ggg acc    1104
Gly Trp Asp Ala His Thr Thr Cys Gln Ala Leu Gly Val Cys Gly Thr
        355                 360                 365 atg tcc agc cct ctc cag tgt atc cac agc ccc gac ctt                1143
Met Ser Ser Pro Leu Gln Cys Ile His Ser Pro Asp Leu
    370                 375                 380

<210> SEQ ID NO 2
<211> LENGTH: 837
<212> TYPE: DNA
<213> ORGANISM: Homo sapiens
<220> FEATURE:
<221> NAME/KEY: CDS
<222> LOCATION: (1)..(837)
<223> OTHER INFORMATION: Coding sequence of the surfactant protein B
      precursor lacking the C-terminal propeptide

<400> SEQUENCE: 2 atg gct gag tca cac ctg ctg cag tgg ctg ctg ctg ctg ctg ccc acg      48
Met Ala Glu Ser His Leu Leu Gln Trp Leu Leu Leu Leu Leu Pro Thr
1               5                   10                  15 ctc tgt ggc cca ggc act gct gcc tgg acc acc tca tcc ttg gcc tgt      96
Leu Cys Gly Pro Gly Thr Ala Ala Trp Thr Thr Ser Ser Leu Ala Cys
            20                  25                  30 gcc cag ggc cct gag ttc tgg tgc caa agc ctg gag caa gca ttg cag     144
Ala Gln Gly Pro Glu Phe Trp Cys Gln Ser Leu Glu Gln Ala Leu Gln
        35                  40                  45 tgc aga gcc cta ggg cat tgc cta cag gaa gtc tgg gga cat gtg gga     192
Cys Arg Ala Leu Gly His Cys Leu Gln Glu Val Trp Gly His Val Gly
    50                  55                  60 gcc gat gac cta tgc caa gag tgt gag gac atc gtc cac atc ctt aac     240
Ala Asp Asp Leu Cys Gln Glu Cys Glu Asp Ile Val His Ile Leu Asn
65                  70                  75                  80 aag atg gcc aag gag gcc att ttc cag gac acg atg agg aag ttc ctg     288
Lys Met Ala Lys Glu Ala Ile Phe Gln Asp Thr Met Arg Lys Phe Leu
                85                  90                  95 gag cag gag tgc aac gtc ctc ccc ttg aag ctg ctc atg ccc cag tgc     336
Glu Gln Glu Cys Asn Val Leu Pro Leu Lys Leu Leu Met Pro Gln Cys
            100                 105                 110 aac caa gtg ctt gac gac tac ttc ccc ctg gtc atc gac tac ttc cag     384
Asn Gln Val Leu Asp Asp Tyr Phe Pro Leu Val Ile Asp Tyr Phe Gln
        115                 120                 125 aac cag act gac tca aac ggc atc tgt atg cac ctg ggc ctg tgc aaa     432
Asn Gln Thr Asp Ser Asn Gly Ile Cys Met His Leu Gly Leu Cys Lys
    130                 135                 140 tcc cgg cag cca gag cca gag cag gag cca ggg atg tca gac ccc ctg     480
Ser Arg Gln Pro Glu Pro Glu Gln Glu Pro Gly Met Ser Asp Pro Leu
145                 150                 155                 160 ccc aaa cct ctg cgg gac cct ctg cca gac cct ctg ctg gac aag ctc     528
Pro Lys Pro Leu Arg Asp Pro Leu Pro Asp Pro Leu Leu Asp Lys Leu
                165                 170                 175 gtc ctc cct gtg ctg ccc ggg gcc ctc cag gcg agg cct ggg cct cac     576
Val Leu Pro Val Leu Pro Gly Ala Leu Gln Ala Arg Pro Gly Pro His
            180                 185                 190 aca cag gat ctc tcc gag cag caa ttc ccc att cct ctc ccc tat tgc     624
Thr Gln Asp Leu Ser Glu Gln Gln Phe Pro Ile Pro Leu Pro Tyr Cys
        195                 200                 205 tgg ctc tgc agg gct ctg atc aag cgg atc caa gcc atg att ccc aag     672
Trp Leu Cys Arg Ala Leu Ile Lys Arg Ile Gln Ala Met Ile Pro Lys
    210                 215                 220
```

-continued

```
ggt gcg cta gct gtg gca gtg gcc cag gtg tgc cgc gtg gta cct ctg      720
Gly Ala Leu Ala Val Ala Val Ala Gln Val Cys Arg Val Val Pro Leu
225                 230                 235                 240 gtg gcg ggc ggc atc tgc cag tgc ctg gct gag cgc tac tcc gtc atc      768
Val Ala Gly Gly Ile Cys Gln Cys Leu Ala Glu Arg Tyr Ser Val Ile
                245                 250                 255 ctg ctc gac acg ctg ctg ggc cgc atg ctg ccc cag ctg gtc tgc cgc      816
Leu Leu Asp Thr Leu Leu Gly Arg Met Leu Pro Gln Leu Val Cys Arg
            260                 265                 270 ctc gtc ctc cgg tgc tcc atg                                          837
Leu Val Leu Arg Cys Ser Met
        275
```

<210> SEQ ID NO 3
<211> LENGTH: 237
<212> TYPE: DNA
<213> ORGANISM: Homo sapiens
<220> FEATURE:
<221> NAME/KEY: CDS
<222> LOCATION: (1)..(237)
<223> OTHER INFORMATION: Coding sequence of the mature surfactant
      protein B

<400> SEQUENCE: 3

```
ttc ccc att cct ctc ccc tat tgc tgg ctc tgc agg gct ctg atc aag       48
Phe Pro Ile Pro Leu Pro Tyr Cys Trp Leu Cys Arg Ala Leu Ile Lys
1               5                   10                  15 cgg atc caa gcc atg att ccc aag ggt gcg cta gct gtg gca gtg gcc       96
Arg Ile Gln Ala Met Ile Pro Lys Gly Ala Leu Ala Val Ala Val Ala
                20                  25                  30 cag gtg tgc cgc gtg gta cct ctg gtg gcg ggc ggc atc tgc cag tgc      144
Gln Val Cys Arg Val Val Pro Leu Val Ala Gly Gly Ile Cys Gln Cys
            35                  40                  45 ctg gct gag cgc tac tcc gtc atc ctg ctc gac acg ctg ctg ggc cgc      192
Leu Ala Glu Arg Tyr Ser Val Ile Leu Leu Asp Thr Leu Leu Gly Arg
        50                  55                  60 atg ctg ccc cag ctg gtc tgc cgc ctc gtc ctc cgg tgc tcc atg          237
Met Leu Pro Gln Leu Val Cys Arg Leu Val Leu Arg Cys Ser Met
65                  70                  75
```

<210> SEQ ID NO 4
<211> LENGTH: 1293
<212> TYPE: DNA
<213> ORGANISM: Homo sapiens
<220> FEATURE:
<221> NAME/KEY: CDS
<222> LOCATION: (1)..(1293)
<223> OTHER INFORMATION: Coding sequence of the single-chain
      urokinase-plasminogen activator

<400> SEQUENCE: 4

```
atg aga gcc ctg ctg gcg cgc ctg ctt ctc tgc gtc ctg gtc gtg agc       48
Met Arg Ala Leu Leu Ala Arg Leu Leu Leu Cys Val Leu Val Val Ser
1               5                   10                  15 gac tcc aaa ggc agc aat gaa ctt cat caa gtt cca tcg aac tgt gac       96
Asp Ser Lys Gly Ser Asn Glu Leu His Gln Val Pro Ser Asn Cys Asp
                20                  25                  30 tgt cta aat gga gga aca tgt gtg tcc aac aag tac ttc tcc aac att      144
Cys Leu Asn Gly Gly Thr Cys Val Ser Asn Lys Tyr Phe Ser Asn Ile
            35                  40                  45 cac tgg tgc aac tgc cca aag aaa ttc gga ggg cag cac tgt gaa ata      192
His Trp Cys Asn Cys Pro Lys Lys Phe Gly Gly Gln His Cys Glu Ile
        50                  55                  60 gat aag tca aaa acc tgc tat gag ggg aat ggt cac ttt tac cga gga      240
Asp Lys Ser Lys Thr Cys Tyr Glu Gly Asn Gly His Phe Tyr Arg Gly
```

-continued

```
                65                  70                  75                  80
aag gcc agc act gac acc atg ggc cgg ccc tgc ctg ccc tgg aac tct       288
Lys Ala Ser Thr Asp Thr Met Gly Arg Pro Cys Leu Pro Trp Asn Ser
                    85                  90                  95 gcc act gtc ctt cag caa acg tac cat gcc cac aga tct gat gct ctt       336
Ala Thr Val Leu Gln Gln Thr Tyr His Ala His Arg Ser Asp Ala Leu
                100                 105                 110 cag ctg ggc ctg ggg aaa cat aat tac tgc agg aac cca gac aac cgg       384
Gln Leu Gly Leu Gly Lys His Asn Tyr Cys Arg Asn Pro Asp Asn Arg
                    115                 120                 125 agg cga ccc tgg tgc tat gtg cag gtg ggc cta aag ccg ctt gtc caa       432
Arg Arg Pro Trp Cys Tyr Val Gln Val Gly Leu Lys Pro Leu Val Gln
        130                 135                 140 gag tgc atg gtg cat gac tgc gca gat gga aaa aag ccc tcc tct cct       480
Glu Cys Met Val His Asp Cys Ala Asp Gly Lys Lys Pro Ser Ser Pro
145                 150                 155                 160 cca gaa gaa tta aaa ttt cag tgt ggc caa aag act ctg agg ccc cgc       528
Pro Glu Glu Leu Lys Phe Gln Cys Gly Gln Lys Thr Leu Arg Pro Arg
                    165                 170                 175 ttt aag att att ggg gga gaa ttc acc acc atc gag aac cag ccc tgg       576
Phe Lys Ile Ile Gly Gly Glu Phe Thr Thr Ile Glu Asn Gln Pro Trp
                180                 185                 190 ttt gcg gcc atc tac agg agg cac cgg ggg ggc tct gtc acc tac gtg       624
Phe Ala Ala Ile Tyr Arg Arg His Arg Gly Gly Ser Val Thr Tyr Val
                    195                 200                 205 tgt gga ggc agc ctc atc agc cct tgc tgg gtg atc agc gcc aca cac       672
Cys Gly Gly Ser Leu Ile Ser Pro Cys Trp Val Ile Ser Ala Thr His
        210                 215                 220 tgc ttc att gat tac cca aag aag gag gac tac atc gtc tac ctg ggt       720
Cys Phe Ile Asp Tyr Pro Lys Lys Glu Asp Tyr Ile Val Tyr Leu Gly
225                 230                 235                 240 cgc tca agg ctt aac tcc aac acg caa ggg gag atg aag ttt gag gtg       768
Arg Ser Arg Leu Asn Ser Asn Thr Gln Gly Glu Met Lys Phe Glu Val
                    245                 250                 255 gaa aac ctc atc cta cac aag gac tac agc gct gac acg ctt gct cac       816
Glu Asn Leu Ile Leu His Lys Asp Tyr Ser Ala Asp Thr Leu Ala His
                260                 265                 270 cac aac gac att gcc ttg ctg aag atc cgt tcc aag gag ggc agg tgt       864
His Asn Asp Ile Ala Leu Leu Lys Ile Arg Ser Lys Glu Gly Arg Cys
                    275                 280                 285 gcg cag cca tcc cgg act ata cag acc atc tgc ctg ccc tcg atg tat       912
Ala Gln Pro Ser Arg Thr Ile Gln Thr Ile Cys Leu Pro Ser Met Tyr
        290                 295                 300 aac gat ccc cag ttt ggc aca agc tgt gag atc act ggc ttt gga aaa       960
Asn Asp Pro Gln Phe Gly Thr Ser Cys Glu Ile Thr Gly Phe Gly Lys
305                 310                 315                 320 gag aat tct acc gac tat ctc tat ccg gag cag ctg aaa atg act gtt      1008
Glu Asn Ser Thr Asp Tyr Leu Tyr Pro Glu Gln Leu Lys Met Thr Val
                    325                 330                 335 gtg aag ctg att tcc cac cgg gag tgt cag cag ccc cac tac tac ggc      1056
Val Lys Leu Ile Ser His Arg Glu Cys Gln Gln Pro His Tyr Tyr Gly
                340                 345                 350 tct gaa gtc acc acc aaa atg ctg tgt gct gct gac cca cag tgg aaa      1104
Ser Glu Val Thr Thr Lys Met Leu Cys Ala Ala Asp Pro Gln Trp Lys
                    355                 360                 365 aca gat tcc tgc cag gga gac tca ggg gga ccc ctc gtc tgt tcc ctc      1152
Thr Asp Ser Cys Gln Gly Asp Ser Gly Gly Pro Leu Val Cys Ser Leu
        370                 375                 380 caa ggc cgc atg act ttg act gga att gtg agc tgg ggc cgt gga tgt      1200
Gln Gly Arg Met Thr Leu Thr Gly Ile Val Ser Trp Gly Arg Gly Cys
```

```
              385                 390                 395                 400
gcc ctg aag gac aag cca ggc gtc tac acg aga gtc tca cac ttc tta              1248
Ala Leu Lys Asp Lys Pro Gly Val Tyr Thr Arg Val Ser His Phe Leu
                405                 410                 415 ccc tgg atc cgc agt cac acc aag gaa gag aat ggc ctg gcc ctc                  1293
Pro Trp Ile Arg Ser His Thr Lys Glu Glu Asn Gly Leu Ala Leu
            420                 425                 430

<210> SEQ ID NO 5
<211> LENGTH: 828
<212> TYPE: DNA
<213> ORGANISM: Homo sapiens
<220> FEATURE:
<221> NAME/KEY: CDS
<222> LOCATION: (1)..(828)
<223> OTHER INFORMATION: Coding sequence of the low molecular weight
      two-chain urokinase-plasminogen activator

<400> SEQUENCE: 5 aag ccc tcc tct cct cca gaa gaa tta aaa ttt cag tgt ggc caa aag              48
Lys Pro Ser Ser Pro Pro Glu Glu Leu Lys Phe Gln Cys Gly Gln Lys
1               5                   10                  15 act ctg agg ccc cgc ttt aag att att ggg gga gaa ttc acc acc atc              96
Thr Leu Arg Pro Arg Phe Lys Ile Ile Gly Gly Glu Phe Thr Thr Ile
            20                  25                  30 gag aac cag ccc tgg ttt gcg gcc atc tac agg agg cac cgg ggg ggc              144
Glu Asn Gln Pro Trp Phe Ala Ala Ile Tyr Arg Arg His Arg Gly Gly
        35                  40                  45 tct gtc acc tac gtg tgt gga ggc agc ctc atc agc cct tgc tgg gtg              192
Ser Val Thr Tyr Val Cys Gly Gly Ser Leu Ile Ser Pro Cys Trp Val
    50                  55                  60 atc agc gcc aca cac tgc ttc att gat tac cca aag aag gag gac tac              240
Ile Ser Ala Thr His Cys Phe Ile Asp Tyr Pro Lys Lys Glu Asp Tyr
65                  70                  75                  80 atc gtc tac ctg ggt cgc tca agg ctt aac tcc aac acg caa ggg gag              288
Ile Val Tyr Leu Gly Arg Ser Arg Leu Asn Ser Asn Thr Gln Gly Glu
                85                  90                  95 atg aag ttt gag gtg gaa aac ctc atc cta cac aag gac tac agc gct              336
Met Lys Phe Glu Val Glu Asn Leu Ile Leu His Lys Asp Tyr Ser Ala
            100                 105                 110 gac acg ctt gct cac cac aac gac att gcc ttg ctg aag atc cgt tcc              384
Asp Thr Leu Ala His His Asn Asp Ile Ala Leu Leu Lys Ile Arg Ser
        115                 120                 125 aag gag ggc agg tgt gcg cag cca tcc cgg act ata cag acc atc tgc              432
Lys Glu Gly Arg Cys Ala Gln Pro Ser Arg Thr Ile Gln Thr Ile Cys
    130                 135                 140 ctg ccc tcg atg tat aac gat ccc cag ttt ggc aca agc tgt gag atc              480
Leu Pro Ser Met Tyr Asn Asp Pro Gln Phe Gly Thr Ser Cys Glu Ile
145                 150                 155                 160 act ggc ttt gga aaa gag aat tct acc gac tat ctc tat ccg gag cag              528
Thr Gly Phe Gly Lys Glu Asn Ser Thr Asp Tyr Leu Tyr Pro Glu Gln
                165                 170                 175 ctg aaa atg act gtt gtg aag ctg att tcc cac cgg gag tgt cag cag              576
Leu Lys Met Thr Val Val Lys Leu Ile Ser His Arg Glu Cys Gln Gln
            180                 185                 190 ccc cac tac tac ggc tct gaa gtc acc acc aaa atg ctg tgt gct gct              624
Pro His Tyr Tyr Gly Ser Glu Val Thr Thr Lys Met Leu Cys Ala Ala
        195                 200                 205 gac cca cag tgg aaa aca gat tcc tgc cag gga gac tca ggg gga ccc              672
Asp Pro Gln Trp Lys Thr Asp Ser Cys Gln Gly Asp Ser Gly Gly Pro
    210                 215                 220 ctc gtc tgt tcc ctc caa ggc cgc atg act ttg act gga att gtg agc              720
Leu Val Cys Ser Leu Gln Gly Arg Met Thr Leu Thr Gly Ile Val Ser
```

```
Leu Val Cys Ser Leu Gln Gly Arg Met Thr Leu Thr Gly Ile Val Ser
225                 230                 235                 240 tgg ggc cgt gga tgt gcc ctg aag gac aag cca ggc gtc tac acg aga      768
Trp Gly Arg Gly Cys Ala Leu Lys Asp Lys Pro Gly Val Tyr Thr Arg
                245                 250                 255 gtc tca cac ttc tta ccc tgg atc cgc agt cac acc aag gaa gag aat      816
Val Ser His Phe Leu Pro Trp Ile Arg Ser His Thr Lys Glu Glu Asn
            260                 265                 270 ggc ctg gcc ctc                                                       828
Gly Leu Ala Leu
        275

<210> SEQ ID NO 6
<211> LENGTH: 1671
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(837)
<223> OTHER INFORMATION: Coding sequence of the surfactant protein B
      precursor lacking the C-terminal propeptide
<220> FEATURE:
<221> NAME/KEY: CDS
<222> LOCATION: (838)..(843)
<223> OTHER INFORMATION: Linker
<220> FEATURE:
<221> NAME/KEY: CDS
<222> LOCATION: (844)..(1671)
<223> OTHER INFORMATION: Coding sequence of the low molecular weight
      two-chain urokinase-plasminogen activator

<400> SEQUENCE: 6 atg gct gag tca cac ctg ctg cag tgg ctg ctg ctg ctg ctg ccc acg       48
Met Ala Glu Ser His Leu Leu Gln Trp Leu Leu Leu Leu Leu Pro Thr
1               5                   10                  15 ctc tgt ggc cca ggc act gct gcc tgg acc acc tca tcc ttg gcc tgt       96
Leu Cys Gly Pro Gly Thr Ala Ala Trp Thr Thr Ser Ser Leu Ala Cys
                20                  25                  30 gcc cag ggc cct gag ttc tgg tgc caa agc ctg gag caa gca ttg cag      144
Ala Gln Gly Pro Glu Phe Trp Cys Gln Ser Leu Glu Gln Ala Leu Gln
            35                  40                  45 tgc aga gcc cta ggg cat tgc cta cag gaa gtc tgg gga cat gtg gga      192
Cys Arg Ala Leu Gly His Cys Leu Gln Glu Val Trp Gly His Val Gly
        50                  55                  60 gcc gat gac cta tgc caa gag tgt gag gac atc gtc cac atc ctt aac      240
Ala Asp Asp Leu Cys Gln Glu Cys Glu Asp Ile Val His Ile Leu Asn
65                  70                  75                  80 aag atg gcc aag gag gcc att ttc cag gac acg atg agg aag ttc ctg      288
Lys Met Ala Lys Glu Ala Ile Phe Gln Asp Thr Met Arg Lys Phe Leu
                85                  90                  95 gag cag gag tgc aac gtc ctc ccc ttg aag ctg ctc atg ccc cag tgc      336
Glu Gln Glu Cys Asn Val Leu Pro Leu Lys Leu Leu Met Pro Gln Cys
            100                 105                 110 aac caa gtg ctt gac gac tac ttc ccc ctg gtc atc gac tac ttc cag      384
Asn Gln Val Leu Asp Asp Tyr Phe Pro Leu Val Ile Asp Tyr Phe Gln
        115                 120                 125 aac cag act gac tca aac ggc atc tgt atg cac ctg ggc ctg tgc aaa      432
Asn Gln Thr Asp Ser Asn Gly Ile Cys Met His Leu Gly Leu Cys Lys
    130                 135                 140 tcc cgg cag cca gag cca gag cag gag cca ggg atg tca gac ccc ctg      480
Ser Arg Gln Pro Glu Pro Glu Gln Glu Pro Gly Met Ser Asp Pro Leu
145                 150                 155                 160
```

```
ccc aaa cct ctg cgg gac cct ctg cca gac cct ctg ctg gac aag ctc      528
Pro Lys Pro Leu Arg Asp Pro Leu Pro Asp Pro Leu Leu Asp Lys Leu
            165                 170                 175 gtc ctc cct gtg ctg ccc ggg gcc ctc cag gcg agg cct ggg cct cac      576
Val Leu Pro Val Leu Pro Gly Ala Leu Gln Ala Arg Pro Gly Pro His
            180                 185                 190 aca cag gat ctc tcc gag cag caa ttc ccc att cct ctc ccc tat tgc      624
Thr Gln Asp Leu Ser Glu Gln Gln Phe Pro Ile Pro Leu Pro Tyr Cys
            195                 200                 205 tgg ctc tgc agg gct ctg atc aag cgg atc caa gcc atg att ccc aag      672
Trp Leu Cys Arg Ala Leu Ile Lys Arg Ile Gln Ala Met Ile Pro Lys
            210                 215                 220 ggt gcg cta gct gtg gca gtg gcc cag gtg tgc cgc gtg gta cct ctg      720
Gly Ala Leu Ala Val Ala Val Ala Gln Val Cys Arg Val Val Pro Leu
225                 230                 235                 240 gtg gcg ggc ggc atc tgc cag tgc ctg gct gag cgc tac tcc gtc atc      768
Val Ala Gly Gly Ile Cys Gln Cys Leu Ala Glu Arg Tyr Ser Val Ile
                245                 250                 255 ctg ctc gac acg ctg ctg ggc cgc atg ctg ccc cag ctg gtc tgc cgc      816
Leu Leu Asp Thr Leu Leu Gly Arg Met Leu Pro Gln Leu Val Cys Arg
                260                 265                 270 ctc gtc ctc cgg tgc tcc atg aag ctt aag ccc tct tct cct cca gaa      864
Leu Val Leu Arg Cys Ser Met Lys Leu Lys Pro Ser Ser Pro Pro Glu
            275                 280                 285 gaa tta aaa ttt cag tgt ggc caa aag act ctg agg ccc cgc ttt aag      912
Glu Leu Lys Phe Gln Cys Gly Gln Lys Thr Leu Arg Pro Arg Phe Lys
            290                 295                 300 att att ggg gga gaa ttc acc acc atc gag aac cag ccc tgg ttt gcg      960
Ile Ile Gly Gly Glu Phe Thr Thr Ile Glu Asn Gln Pro Trp Phe Ala
305                 310                 315                 320 gcc atc tac agg agg cac cgg ggg ggc tct gtc acc tac gtg tgt gga     1008
Ala Ile Tyr Arg Arg His Arg Gly Gly Ser Val Thr Tyr Val Cys Gly
                325                 330                 335 ggc agc ctc atc agc cct tgc tgg gtg atc agc gcc aca cac tgc ttc     1056
Gly Ser Leu Ile Ser Pro Cys Trp Val Ile Ser Ala Thr His Cys Phe
                340                 345                 350 att gat tac cca aag aag gag gac tac atc gtc tac ctg ggt cgc tca     1104
Ile Asp Tyr Pro Lys Lys Glu Asp Tyr Ile Val Tyr Leu Gly Arg Ser
            355                 360                 365 agg ctt aac tcc aac acg caa ggg gag atg aag ttt gag gtg gaa aac     1152
Arg Leu Asn Ser Asn Thr Gln Gly Glu Met Lys Phe Glu Val Glu Asn
            370                 375                 380 ctc atc cta cac aag gac tac agc gct gac acg ctt gct cac cac aac     1200
Leu Ile Leu His Lys Asp Tyr Ser Ala Asp Thr Leu Ala His His Asn
385                 390                 395                 400 gac att gcc ttg ctg aag atc cgt tcc aag gag ggc agg tgt gcg cag     1248
Asp Ile Ala Leu Leu Lys Ile Arg Ser Lys Glu Gly Arg Cys Ala Gln
                405                 410                 415 cca tcc cgg act ata cag acc atc tgc ctg ccc tcg atg tat aac gat     1296
Pro Ser Arg Thr Ile Gln Thr Ile Cys Leu Pro Ser Met Tyr Asn Asp
                420                 425                 430 ccc cag ttt ggc aca agc tgt gag atc act ggc ttt gga aaa gag aat     1344
Pro Gln Phe Gly Thr Ser Cys Glu Ile Thr Gly Phe Gly Lys Glu Asn
            435                 440                 445 tct acc gac tat ctc tat ccg gag cag ctg aaa atg act gtt gtg aag     1392
Ser Thr Asp Tyr Leu Tyr Pro Glu Gln Leu Lys Met Thr Val Val Lys
450                 455                 460 ctg att tcc cac cgg gag tgt cag cag ccc cac tac tac ggc tct gaa     1440
Leu Ile Ser His Arg Glu Cys Gln Gln Pro His Tyr Tyr Gly Ser Glu
465                 470                 475                 480
```

```
gtc acc acc aaa atg ctg tgt gct gct gac cca cag tgg aaa aca gat    1488
Val Thr Thr Lys Met Leu Cys Ala Ala Asp Pro Gln Trp Lys Thr Asp
            485                 490                 495 tcc tgc cag gga gac tca ggg gga ccc ctc gtc tgt tcc ctc caa ggc    1536
Ser Cys Gln Gly Asp Ser Gly Gly Pro Leu Val Cys Ser Leu Gln Gly
        500                 505                 510 cgc atg act ttg act gga att gtg agc tgg ggc cgt gga tgt gcc ctg    1584
Arg Met Thr Leu Thr Gly Ile Val Ser Trp Gly Arg Gly Cys Ala Leu
        515                 520                 525 aag gac aag cca ggc gtc tac acg aga gtc tca cac ttc tta ccc tgg    1632
Lys Asp Lys Pro Gly Val Tyr Thr Arg Val Ser His Phe Leu Pro Trp
    530                 535                 540 atc cgc agt cac acc aag gaa gag aat ggc ctg gcc ctc                1671
Ile Arg Ser His Thr Lys Glu Glu Asn Gly Leu Ala Leu
545                 550                 555

<210> SEQ ID NO 7
<211> LENGTH: 1674
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(837)
<223> OTHER INFORMATION: Coding sequence of the surfactant protein B
      precursor lacking the C-terminal propeptide
<220> FEATURE:
<221> NAME/KEY: CDS
<222> LOCATION: (838)..(846)
<223> OTHER INFORMATION: Linker
<220> FEATURE:
<221> NAME/KEY: CDS
<222> LOCATION: (847)..(1674)
<223> OTHER INFORMATION: Coding sequence of the low molecular weight
      two-chain urokinase-plasminogen activator

<400> SEQUENCE: 7 atg gct gag tca cac ctg ctg cag tgg ctg ctg ctg ctg ctg ccc acg      48
Met Ala Glu Ser His Leu Leu Gln Trp Leu Leu Leu Leu Leu Pro Thr
1               5                   10                  15 ctc tgt ggc cca ggc act gct gcc tgg acc acc tca tcc ttg gcc tgt      96
Leu Cys Gly Pro Gly Thr Ala Ala Trp Thr Thr Ser Ser Leu Ala Cys
                20                  25                  30 gcc cag ggc cct gag ttc tgg tgc caa agc ctg gag caa gca ttg cag     144
Ala Gln Gly Pro Glu Phe Trp Cys Gln Ser Leu Glu Gln Ala Leu Gln
            35                  40                  45 tgc aga gcc cta ggg cat tgc cta cag gaa gtc tgg gga cat gtg gga     192
Cys Arg Ala Leu Gly His Cys Leu Gln Glu Val Trp Gly His Val Gly
        50                  55                  60 gcc gat gac cta tgc caa gag tgt gag gac atc gtc cac atc ctt aac     240
Ala Asp Asp Leu Cys Gln Glu Cys Glu Asp Ile Val His Ile Leu Asn
65                  70                  75                  80 aag atg gcc aag gag gcc att ttc cag gac acg atg agg aag ttc ctg     288
Lys Met Ala Lys Glu Ala Ile Phe Gln Asp Thr Met Arg Lys Phe Leu
                85                  90                  95 gag cag gag tgc aac gtc ctc ccc ttg aag ctc ctc atg ccc cag tgc     336
Glu Gln Glu Cys Asn Val Leu Pro Leu Lys Leu Leu Met Pro Gln Cys
                100                 105                 110 aac caa gtg ctt gac gac tac ttc ccc ctg gtc atc gac tac ttc cag     384
Asn Gln Val Leu Asp Asp Tyr Phe Pro Leu Val Ile Asp Tyr Phe Gln
            115                 120                 125 aac cag act gac tca aac ggc atc tgt atg cac ctg ggc ctg tgc aaa     432
Asn Gln Thr Asp Ser Asn Gly Ile Cys Met His Leu Gly Leu Cys Lys
        130                 135                 140
```

```
tcc cgg cag cca gag cca gag cag gag cca ggg atg tca gac ccc ctg      480
Ser Arg Gln Pro Glu Pro Glu Gln Glu Pro Gly Met Ser Asp Pro Leu
145                 150                 155                 160 ccc aaa cct ctg cgg gac cct ctg cca gac cct ctg ctg gac aag ctc      528
Pro Lys Pro Leu Arg Asp Pro Leu Pro Asp Pro Leu Leu Asp Lys Leu
                165                 170                 175 gtc ctc cct gtg ctg ccc ggg gcc ctc cag gcg agg cct ggg cct cac      576
Val Leu Pro Val Leu Pro Gly Ala Leu Gln Ala Arg Pro Gly Pro His
            180                 185                 190 aca cag gat ctc tcc gag cag caa ttc ccc att cct ctc ccc tat tgc      624
Thr Gln Asp Leu Ser Glu Gln Gln Phe Pro Ile Pro Leu Pro Tyr Cys
        195                 200                 205 tgg ctc tgc agg gct ctg atc aag cgg atc caa gcc atg att ccc aag      672
Trp Leu Cys Arg Ala Leu Ile Lys Arg Ile Gln Ala Met Ile Pro Lys
    210                 215                 220 ggt gcg cta gct gtg gca gtg gcc cag gtg tgc cgc gtg gta cct ctg      720
Gly Ala Leu Ala Val Ala Val Ala Gln Val Cys Arg Val Val Pro Leu
225                 230                 235                 240 gtg gcg ggc ggc atc tgc cag tgc ctg gct gag cgc tac tcc gtc atc      768
Val Ala Gly Gly Ile Cys Gln Cys Leu Ala Glu Arg Tyr Ser Val Ile
                245                 250                 255 ctg ctc gac acg ctg ctg ggc cgc atg ctg ccc cag ctg gtc tgc cgc      816
Leu Leu Asp Thr Leu Leu Gly Arg Met Leu Pro Gln Leu Val Cys Arg
            260                 265                 270 ctc gtc ctc cgg tgc tcc atg cag ata tct aag ccc tcc tct cct cca      864
Leu Val Leu Arg Cys Ser Met Gln Ile Ser Lys Pro Ser Ser Pro Pro
        275                 280                 285 gaa gaa tta aaa ttt cag tgt ggc caa aag act ctg agg ccc cgc ttt      912
Glu Glu Leu Lys Phe Gln Cys Gly Gln Lys Thr Leu Arg Pro Arg Phe
    290                 295                 300 aag att att ggg gga gaa ttc acc acc atc gag aac cag ccc tgg ttt      960
Lys Ile Ile Gly Gly Glu Phe Thr Thr Ile Glu Asn Gln Pro Trp Phe
305                 310                 315                 320 gcg gcc atc tac agg agg cac cgg ggg ggc tct gtc acc tac gtg tgt     1008
Ala Ala Ile Tyr Arg Arg His Arg Gly Gly Ser Val Thr Tyr Val Cys
                325                 330                 335 gga ggc agc ctc atc agc cct tgc tgg gtg atc agc gcc aca cac tgc     1056
Gly Gly Ser Leu Ile Ser Pro Cys Trp Val Ile Ser Ala Thr His Cys
            340                 345                 350 ttc att gat tac cca aag aag gag gac tac atc gtc tac ctg ggt cgc     1104
Phe Ile Asp Tyr Pro Lys Lys Glu Asp Tyr Ile Val Tyr Leu Gly Arg
        355                 360                 365 tca agg ctt aac tcc aac acg caa ggg gag atg aag ttt gag gtg gaa     1152
Ser Arg Leu Asn Ser Asn Thr Gln Gly Glu Met Lys Phe Glu Val Glu
    370                 375                 380 aac ctc atc cta cac aag gac tac agc gct gac acg ctt gct cac cac     1200
Asn Leu Ile Leu His Lys Asp Tyr Ser Ala Asp Thr Leu Ala His His
385                 390                 395                 400 aac gac att gcc ttg ctg aag atc cgt tcc aag gag ggc agg tgt gcg     1248
Asn Asp Ile Ala Leu Leu Lys Ile Arg Ser Lys Glu Gly Arg Cys Ala
                405                 410                 415 cag cca tcc cgg act ata cag acc atc tgc ctg ccc tcg atg tat aac     1296
Gln Pro Ser Arg Thr Ile Gln Thr Ile Cys Leu Pro Ser Met Tyr Asn
            420                 425                 430 gat ccc cag ttt ggc aca agc tgt gag atc act ggc ttt gga aaa gag     1344
Asp Pro Gln Phe Gly Thr Ser Cys Glu Ile Thr Gly Phe Gly Lys Glu
        435                 440                 445 aat tct acc gac tat ctc tat ccg gag cag ctg aaa atg act gtt gtg     1392
Asn Ser Thr Asp Tyr Leu Tyr Pro Glu Gln Leu Lys Met Thr Val Val
    450                 455                 460
```

| | | |
|---|---|---|
| aag ctg att tcc cac cgg gag tgt cag cag ccc cac tac tac ggc tct<br>Lys Leu Ile Ser His Arg Glu Cys Gln Gln Pro His Tyr Tyr Gly Ser<br>465                     470                            475                            480 | | 1440 |
| gaa gtc acc acc aaa atg ctg tgt gct gct gac cca cag tgg aaa aca<br>Glu Val Thr Thr Lys Met Leu Cys Ala Ala Asp Pro Gln Trp Lys Thr<br>                            485                            490                            495 | | 1488 |
| gat tcc tgc cag gga gac tca ggg gga ccc ctc gtc tgt tcc ctc caa<br>Asp Ser Cys Gln Gly Asp Ser Gly Gly Pro Leu Val Cys Ser Leu Gln<br>                     500                            505                            510 | | 1536 |
| ggc cgc atg act ttg act gga att gtg agc tgg ggc cgt gga tgt gcc<br>Gly Arg Met Thr Leu Thr Gly Ile Val Ser Trp Gly Arg Gly Cys Ala<br>               515                            520                            525 | | 1584 |
| ctg aag gac aag cca ggc gtc tac acg aga gtc tca cac ttc tta ccc<br>Leu Lys Asp Lys Pro Gly Val Tyr Thr Arg Val Ser His Phe Leu Pro<br>530                     535                            540 | | 1632 |
| tgg atc cgc agt cac acc aag gaa gag aat ggc ctg gcc ctc<br>Trp Ile Arg Ser His Thr Lys Glu Glu Asn Gly Leu Ala Leu<br>545                     550                            555 | | 1674 |

<210> SEQ ID NO 8
<211> LENGTH: 591
<212> TYPE: DNA
<213> ORGANISM: Homo sapiens
<220> FEATURE:
<221> NAME/KEY: CDS
<222> LOCATION: (1)..(591)
<223> OTHER INFORMATION: Coding sequence of the surfactant protein C
      precursor

<400> SEQUENCE: 8

| | | |
|---|---|---|
| atg gat gtg ggc agc aaa gag gtc ctg atg gag agc ccg ccg gac tac<br>Met Asp Val Gly Ser Lys Glu Val Leu Met Glu Ser Pro Pro Asp Tyr<br>1                     5                             10                            15 | | 48 |
| tcc gca gct ccc cgg ggc cga ttt ggc att ccc tgc tgc cca gtg cac<br>Ser Ala Ala Pro Arg Gly Arg Phe Gly Ile Pro Cys Cys Pro Val His<br>                     20                            25                            30 | | 96 |
| ctg aaa cgc ctt ctt atc gtg gtg gtg gtg gtc ctc atc gtc gtg<br>Leu Lys Arg Leu Leu Ile Val Val Val Val Val Leu Ile Val Val<br>               35                            40                            45 | | 144 |
| gtg att gtg gga gcc ctg ctc atg ggt ctc cac atg agc cag aaa cac<br>Val Ile Val Gly Ala Leu Leu Met Gly Leu His Met Ser Gln Lys His<br>50                     55                            60 | | 192 |
| acg gag atg gtt ctg gag atg agc att ggg gcg ccg gaa gcc cag caa<br>Thr Glu Met Val Leu Glu Met Ser Ile Gly Ala Pro Glu Ala Gln Gln<br>65                     70                            75                            80 | | 240 |
| cgc ctg gcc ctg agt gag cac ctg gtt acc act gcc acc ttc tcc atc<br>Arg Leu Ala Leu Ser Glu His Leu Val Thr Thr Ala Thr Phe Ser Ile<br>                            85                            90                            95 | | 288 |
| ggc tcc act ggc ctc gtg gtg tat gac tac cag cag ctg ctg atc gcc<br>Gly Ser Thr Gly Leu Val Val Tyr Asp Tyr Gln Gln Leu Leu Ile Ala<br>                     100                           105                            110 | | 336 |
| tac aag cca gcc cct ggc acc tgc tgc tac atc atg aag ata gct cca<br>Tyr Lys Pro Ala Pro Gly Thr Cys Cys Tyr Ile Met Lys Ile Ala Pro<br>               115                           120                           125 | | 384 |
| gag agc atc ccc agt ctt gag gct ctc act aga aaa gtc cac aac ttc<br>Glu Ser Ile Pro Ser Leu Glu Ala Leu Thr Arg Lys Val His Asn Phe<br>130                     135                           140 | | 432 |
| cag atg gaa tgc tct ctg cag gcc aag ccc gca gtg cct acg tct aag<br>Gln Met Glu Cys Ser Leu Gln Ala Lys Pro Ala Val Pro Thr Ser Lys<br>145                     150                           155                            160 | | 480 |
| ctg ggc cag gca gag ggg cga gat gca ggc tca gca ccc tcc gga ggg<br>Leu Gly Gln Ala Glu Gly Arg Asp Ala Gly Ser Ala Pro Ser Gly Gly | | 528 |

```
                       165                 170                 175
gac ccg gcc ttc ctg ggc atg gcc gtg agc acc ctg tgt ggc gag gtg      576
Asp Pro Ala Phe Leu Gly Met Ala Val Ser Thr Leu Cys Gly Glu Val
            180                 185                 190 ccg ctc tac tac atc                                                  591
Pro Leu Tyr Tyr Ile
        195

<210> SEQ ID NO 9
<211> LENGTH: 174
<212> TYPE: DNA
<213> ORGANISM: Homo sapiens
<220> FEATURE:
<221> NAME/KEY: CDS
<222> LOCATION: (1)..(174)
<223> OTHER INFORMATION: Coding sequence of the surfactant protein C
      precursor lacking the C-terminal propeptide

<400> SEQUENCE: 9 atg gat gtg ggc agc aaa gag gtc ctg atg gag agc ccg ccg gac tac      48
Met Asp Val Gly Ser Lys Glu Val Leu Met Glu Ser Pro Pro Asp Tyr
1               5                   10                  15 tcc gca gct ccc cgg ggc cga ttt ggc att ccc tgc tgc cca gtg cac      96
Ser Ala Ala Pro Arg Gly Arg Phe Gly Ile Pro Cys Cys Pro Val His
            20                  25                  30 ctg aaa cgc ctt ctt atc gtg gtg gtg gtg gtg gtc ctc atc gtc gtg     144
Leu Lys Arg Leu Leu Ile Val Val Val Val Val Leu Ile Val Val
        35                  40                  45 gtg att gtg gga gcc ctg ctc atg ggt ctc                             174
Val Ile Val Gly Ala Leu Leu Met Gly Leu
    50                  55

<210> SEQ ID NO 10
<211> LENGTH: 105
<212> TYPE: DNA
<213> ORGANISM: Homo sapiens
<220> FEATURE:
<221> NAME/KEY: CDS
<222> LOCATION: (1)..(105)
<223> OTHER INFORMATION: Coding sequence of the mature surfactant
      protein C

<400> SEQUENCE: 10 ttt ggc att ccc tgc tgc cca gtg cac ctg aaa cgc ctt ctt atc gtg      48
Phe Gly Ile Pro Cys Cys Pro Val His Leu Lys Arg Leu Leu Ile Val
1               5                   10                  15 gtg gtg gtg gtg gtc ctc atc gtc gtg gtg att gtg gga gcc ctg ctc      96
Val Val Val Val Val Leu Ile Val Val Val Ile Val Gly Ala Leu Leu
            20                  25                  30 atg ggt ctc                                                         105
Met Gly Leu
        35

<210> SEQ ID NO 11
<211> LENGTH: 1686
<212> TYPE: DNA
<213> ORGANISM: Homo sapiens
<220> FEATURE:
<221> NAME/KEY: CDS
<222> LOCATION: (1)..(1686)
<223> OTHER INFORMATION: Coding sequence of the tissue-plasminogen
      activator

<400> SEQUENCE: 11 atg gat gca atg aag aga ggg ctc tgc tgt gtg ctg ctg ctg tgt gga      48
Met Asp Ala Met Lys Arg Gly Leu Cys Cys Val Leu Leu Leu Cys Gly
1               5                   10                  15
```

```
gca gtc ttc gtt tcg ccc agc cag gaa atc cat gcc cga ttc aga aga      96
Ala Val Phe Val Ser Pro Ser Gln Glu Ile His Ala Arg Phe Arg Arg
         20                  25                  30 gga gcc aga tct tac caa gtg atc tgc aga gat gaa aaa acg cag atg     144
Gly Ala Arg Ser Tyr Gln Val Ile Cys Arg Asp Glu Lys Thr Gln Met
             35                  40                  45 ata tac cag caa cat cag tca tgg ctg cgc cct gtg ctc aga agc aac     192
Ile Tyr Gln Gln His Gln Ser Trp Leu Arg Pro Val Leu Arg Ser Asn
 50                  55                  60 cgg gtg gaa tat tgc tgg tgc aac agt ggc agg gca cag tgc cac tca     240
Arg Val Glu Tyr Cys Trp Cys Asn Ser Gly Arg Ala Gln Cys His Ser
 65                  70                  75                  80 gtg cct gtc aaa agt tgc agc gag cca agg tgt ttc aac ggg ggc acc     288
Val Pro Val Lys Ser Cys Ser Glu Pro Arg Cys Phe Asn Gly Gly Thr
                 85                  90                  95 tgc cag cag gcc ctg tac ttc tca gat ttc gtg tgc cag tgc ccc gaa     336
Cys Gln Gln Ala Leu Tyr Phe Ser Asp Phe Val Cys Gln Cys Pro Glu
             100                 105                 110 gga ttt gct ggg aag tgc tgt gaa ata gat acc agg gcc acg tgc tac     384
Gly Phe Ala Gly Lys Cys Cys Glu Ile Asp Thr Arg Ala Thr Cys Tyr
         115                 120                 125 gag gac cag ggc atc agc tac agg ggc acg tgg agc aca gcg gag agt     432
Glu Asp Gln Gly Ile Ser Tyr Arg Gly Thr Trp Ser Thr Ala Glu Ser
130                 135                 140 ggc gcc gag tgc acc aac tgg aac agc agc gcg ttg gcc cag aag ccc     480
Gly Ala Glu Cys Thr Asn Trp Asn Ser Ser Ala Leu Ala Gln Lys Pro
145                 150                 155                 160 tac agc ggg cgg agg cca gat gcc atc agg ctg ggc ctg ggg aac cac     528
Tyr Ser Gly Arg Arg Pro Asp Ala Ile Arg Leu Gly Leu Gly Asn His
                 165                 170                 175 aac tac tgc aga aac cca gat cga gac tca aag ccc tgg tgc tac gtc     576
Asn Tyr Cys Arg Asn Pro Asp Arg Asp Ser Lys Pro Trp Cys Tyr Val
             180                 185                 190 ttt aag gcg ggg aag tac agc tca gag ttc tgc agc acc cct gcc tgc     624
Phe Lys Ala Gly Lys Tyr Ser Ser Glu Phe Cys Ser Thr Pro Ala Cys
         195                 200                 205 tct gag gga aac agt gac tgc tac ttt ggg aat ggg tca gcc tac cgt     672
Ser Glu Gly Asn Ser Asp Cys Tyr Phe Gly Asn Gly Ser Ala Tyr Arg
210                 215                 220 ggc acg cac agc ctc acc gag tcg ggt gcc tcc tgc ctc ccg tgg aat     720
Gly Thr His Ser Leu Thr Glu Ser Gly Ala Ser Cys Leu Pro Trp Asn
225                 230                 235                 240 tcc atg atc ctg ata ggc aag gtt tac aca gca cag aac ccc agt gcc     768
Ser Met Ile Leu Ile Gly Lys Val Tyr Thr Ala Gln Asn Pro Ser Ala
                 245                 250                 255 cag gca ctg ggc ctg ggc aaa cat aat tac tgc cgg aat cct gat ggg     816
Gln Ala Leu Gly Leu Gly Lys His Asn Tyr Cys Arg Asn Pro Asp Gly
             260                 265                 270 gat gcc aag ccc tgg tgc cac gtg ctg aag aac cgc agg ctg acg tgg     864
Asp Ala Lys Pro Trp Cys His Val Leu Lys Asn Arg Arg Leu Thr Trp
         275                 280                 285 gag tac tgt gat gtg ccc tcc tgc tcc acc tgc ggc ctg aga cag tac     912
Glu Tyr Cys Asp Val Pro Ser Cys Ser Thr Cys Gly Leu Arg Gln Tyr
290                 295                 300 agc cag cct cag ttt cgc atc aaa gga ggg ctc ttc gcc gac atc gcc     960
Ser Gln Pro Gln Phe Arg Ile Lys Gly Gly Leu Phe Ala Asp Ile Ala
305                 310                 315                 320 tcc cac ccc tgg cag gct gcc atc ttt gcc aag cac agg agg tcg ccc    1008
Ser His Pro Trp Gln Ala Ala Ile Phe Ala Lys His Arg Arg Ser Pro
                 325                 330                 335
```

| | | | | | | | | | | | | | | | |
|---|---|---|---|---|---|---|---|---|---|---|---|---|---|---|---|
| gga | gag | cgg | ttc | ctg | tgc | ggg | ggc | ata | ctc | atc | agc | tcc | tgc | tgg | att | 1056 |
| Gly | Glu | Arg | Phe | Leu | Cys | Gly | Gly | Ile | Leu | Ile | Ser | Ser | Cys | Trp | Ile |
| | | | 340 | | | | | 345 | | | | | 350 | | |

```
gga gag cgg ttc ctg tgc ggg ggc ata ctc atc agc tcc tgc tgg att      1056
Gly Glu Arg Phe Leu Cys Gly Gly Ile Leu Ile Ser Ser Cys Trp Ile
            340                 345                 350 ctc tct gcc gcc cac tgc ttc cag gag agg ttt ccg ccc cac cac ctg      1104
Leu Ser Ala Ala His Cys Phe Gln Glu Arg Phe Pro Pro His His Leu
                355                 360                 365 acg gtg atc ttg ggc aga aca tac cgg gtg gtc cct ggc gag gag gag      1152
Thr Val Ile Leu Gly Arg Thr Tyr Arg Val Val Pro Gly Glu Glu Glu
370                 375                 380 cag aaa ttt gaa gtc gaa aaa tac att gtc cat aag gaa ttc gat gat      1200
Gln Lys Phe Glu Val Glu Lys Tyr Ile Val His Lys Glu Phe Asp Asp
385                 390                 395                 400 gac act tac gac aat gac att gcg ctg ctg cag ctg aaa tcg gat tcg      1248
Asp Thr Tyr Asp Asn Asp Ile Ala Leu Leu Gln Leu Lys Ser Asp Ser
                405                 410                 415 tcc cgc tgt gcc cag gag agc agc gtg gtc cgc act gtg tgc ctt ccc      1296
Ser Arg Cys Ala Gln Glu Ser Ser Val Val Arg Thr Val Cys Leu Pro
                420                 425                 430 ccg gcg gac ctg cag ctg ccg gac tgg acg gag tgt gag ctc tcc ggc      1344
Pro Ala Asp Leu Gln Leu Pro Asp Trp Thr Glu Cys Glu Leu Ser Gly
            435                 440                 445 tac ggc aag cat gag gcc ttg tct cct ttc tat tcg gag cgg ctg aag      1392
Tyr Gly Lys His Glu Ala Leu Ser Pro Phe Tyr Ser Glu Arg Leu Lys
450                 455                 460 gag gct cat gtc aga ctg tac cca tcc agc cgc tgc aca tca caa cat      1440
Glu Ala His Val Arg Leu Tyr Pro Ser Ser Arg Cys Thr Ser Gln His
465                 470                 475                 480 tta ctt aac aga aca gtc acc gac aac atg ctg tgt gct gga gac act      1488
Leu Leu Asn Arg Thr Val Thr Asp Asn Met Leu Cys Ala Gly Asp Thr
                485                 490                 495 cgg agc ggc ggg ccc cag gca aac ttg cac gac gcc tgc cag ggc gat      1536
Arg Ser Gly Gly Pro Gln Ala Asn Leu His Asp Ala Cys Gln Gly Asp
            500                 505                 510 tcg gga ggc ccc ctg gtg tgt ctg aac gat ggc cgc atg act ttg gtg      1584
Ser Gly Gly Pro Leu Val Cys Leu Asn Asp Gly Arg Met Thr Leu Val
            515                 520                 525 ggc atc atc agc tgg ggc ctg ggc tgt gga cag aag gat gtc ccg ggt      1632
Gly Ile Ile Ser Trp Gly Leu Gly Cys Gly Gln Lys Asp Val Pro Gly
530                 535                 540 gtg tac acc aag gtt acc aac tac cta gac tgg att cgt gac aac atg      1680
Val Tyr Thr Lys Val Thr Asn Tyr Leu Asp Trp Ile Arg Asp Asn Met
545                 550                 555                 560 cga ccg                                                              1686
Arg Pro <210> SEQ ID NO 12
<211> LENGTH: 1158
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(69)
<223> OTHER INFORMATION: Signal sequence of the surfactant protein B
<220> FEATURE:
<221> NAME/KEY: CDS
<222> LOCATION: (70)..(75)
<223> OTHER INFORMATION: Linker
<220> FEATURE:
<221> NAME/KEY: CDS
<222> LOCATION: (76)..(312)
<223> OTHER INFORMATION: Coding sequence of the mature surfactant
```

```
        protein B
<220> FEATURE:
<221> NAME/KEY: CDS
<222> LOCATION: (313)..(1140)
<223> OTHER INFORMATION: Coding sequence of the low molecular weight
      two-chain urokinase-plasminogen activator
<220> FEATURE:
<221> NAME/KEY: CDS
<222> LOCATION: (1141)..(1158)
<223> OTHER INFORMATION: Hexahistidine affinity tag

<400> SEQUENCE: 12 atg gct gag tca cac ctg ctg cag tgg ctg ctg ctg ctg ccc acg         48
Met Ala Glu Ser His Leu Leu Gln Trp Leu Leu Leu Leu Pro Thr
1               5                   10                  15 ctc tgt ggc cca ggc act gct gcc tgg ttc ccc att cct ctc ccc tat     96
Leu Cys Gly Pro Gly Thr Ala Ala Trp Phe Pro Ile Pro Leu Pro Tyr
            20                  25                  30 tgc tgg ctc tgc agg gct ctg atc aag cgg atc caa gcc atg att ccc    144
Cys Trp Leu Cys Arg Ala Leu Ile Lys Arg Ile Gln Ala Met Ile Pro
        35                  40                  45 aag ggt gcg cta gct gtg gca gtg gcc cag gtg tgc cgc gtg gta cct    192
Lys Gly Ala Leu Ala Val Ala Val Ala Gln Val Cys Arg Val Val Pro
    50                  55                  60 ctg gtg gcg ggc ggc atc tgc cag tgc ctg gct gag cgc tac tcc gtc    240
Leu Val Ala Gly Gly Ile Cys Gln Cys Leu Ala Glu Arg Tyr Ser Val
65                  70                  75                  80 atc ctc ctc gac acg ctg ctg ggc cgc atg ctg ccc cag ctg gtc tgc    288
Ile Leu Leu Asp Thr Leu Leu Gly Arg Met Leu Pro Gln Leu Val Cys
                85                  90                  95 cgc ctc gtc ctc cgg tgc tcc atg aag ccc tcc tct cct cca gaa gaa    336
Arg Leu Val Leu Arg Cys Ser Met Lys Pro Ser Ser Pro Pro Glu Glu
            100                 105                 110 tta aaa ttt cag tgt ggc caa aag act ctg agg ccc cgc ttt aag att    384
Leu Lys Phe Gln Cys Gly Gln Lys Thr Leu Arg Pro Arg Phe Lys Ile
        115                 120                 125 att ggg gga gaa ttc acc acc atc gag aac cag ccc tgg ttt gcg gcc    432
Ile Gly Gly Glu Phe Thr Thr Ile Glu Asn Gln Pro Trp Phe Ala Ala
    130                 135                 140 atc tac agg agg cac cgg ggg ggc tct gtc acc tac gtg tgt gga ggc    480
Ile Tyr Arg Arg His Arg Gly Gly Ser Val Thr Tyr Val Cys Gly Gly
145                 150                 155                 160 agc ctc atc agc cct tgc tgg gtg atc agc gcc aca cac tgc ttc att    528
Ser Leu Ile Ser Pro Cys Trp Val Ile Ser Ala Thr His Cys Phe Ile
                165                 170                 175 gat tac cca aag aag gag gac tac atc gtc tac ctg ggt cgc tca agg    576
Asp Tyr Pro Lys Lys Glu Asp Tyr Ile Val Tyr Leu Gly Arg Ser Arg
            180                 185                 190 ctt aac tcc aac acg caa ggg gag atg aag ttt gag gtg gaa aac ctc    624
Leu Asn Ser Asn Thr Gln Gly Glu Met Lys Phe Glu Val Glu Asn Leu
        195                 200                 205 atc cta cac aag gac tac agc gct gac acg ctt gct cac cac aac gac    672
Ile Leu His Lys Asp Tyr Ser Ala Asp Thr Leu Ala His His Asn Asp
    210                 215                 220 att gcc ttg ctg aag atc cgt tcc aag gag ggc agg tgt gcg cag cca    720
Ile Ala Leu Leu Lys Ile Arg Ser Lys Glu Gly Arg Cys Ala Gln Pro
225                 230                 235                 240 tcc cgg act ata cag acc atc tgc ctg ccc tcg atg tat aac gat ccc    768
Ser Arg Thr Ile Gln Thr Ile Cys Leu Pro Ser Met Tyr Asn Asp Pro
                245                 250                 255 cag ttt ggc aca agc tgt gag atc act ggc ttt gga aaa gag aat tct    816
Gln Phe Gly Thr Ser Cys Glu Ile Thr Gly Phe Gly Lys Glu Asn Ser
            260                 265                 270
```

```
acc gac tat ctc tat ccg gag cag ctg aaa atg act gtt gtg aag ctg      864
Thr Asp Tyr Leu Tyr Pro Glu Gln Leu Lys Met Thr Val Val Lys Leu
        275                 280                 285 att tcc cac cgg gag tgt cag cag ccc cac tac tac ggc tct gaa gtc      912
Ile Ser His Arg Glu Cys Gln Gln Pro His Tyr Tyr Gly Ser Glu Val
        290                 295                 300 acc acc aaa atg ctg tgt gct gct gac cca cag tgg aaa aca gat tcc      960
Thr Thr Lys Met Leu Cys Ala Ala Asp Pro Gln Trp Lys Thr Asp Ser
305                 310                 315                 320 tgc cag gga gac tca ggg gga ccc ctc gtc tgt tcc ctc caa ggc cgc     1008
Cys Gln Gly Asp Ser Gly Gly Pro Leu Val Cys Ser Leu Gln Gly Arg
                325                 330                 335 atg act ttg act gga att gtg agc tgg ggc cgt gga tgt gcc ctg aag     1056
Met Thr Leu Thr Gly Ile Val Ser Trp Gly Arg Gly Cys Ala Leu Lys
            340                 345                 350 gac aag cca ggc gtc tac acg aga gtc tca cac ttc tta ccc tgg atc     1104
Asp Lys Pro Gly Val Tyr Thr Arg Val Ser His Phe Leu Pro Trp Ile
        355                 360                 365 cgc agt cac acc aag gaa gag aat ggc ctg gcc ctc cat cat cat cat     1152
Arg Ser His Thr Lys Glu Glu Asn Gly Leu Ala Leu His His His His
        370                 375                 380 cat cat                                                             1158
His His
385

<210> SEQ ID NO 13
<211> LENGTH: 1149
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(60)
<223> OTHER INFORMATION: Signal sequence of the urokinase plasminogen
      activator
<220> FEATURE:
<221> NAME/KEY: CDS
<222> LOCATION: (61)..(66)
<223> OTHER INFORMATION: Linker
<220> FEATURE:
<221> NAME/KEY: CDS
<222> LOCATION: (67)..(894)
<223> OTHER INFORMATION: Coding sequence of the low molecular weight two
      chain urokinase-plasminogen activator
<220> FEATURE:
<221> NAME/KEY: CDS
<222> LOCATION: (895)..(1131)
<223> OTHER INFORMATION: Coding sequence of the mature surfactant
      protein B
<220> FEATURE:
<221> NAME/KEY: CDS
<222> LOCATION: (1132)..(1149)
<223> OTHER INFORMATION: Hexahistidine affinity tag

<400> SEQUENCE: 13 atg aga gcc ctg ctg gcg cgc ctg ctt ctc tgc gtc ctg gtc gtg agc       48
Met Arg Ala Leu Leu Ala Arg Leu Leu Leu Cys Val Leu Val Val Ser
1               5                  10                  15 gac tcc aaa ggc agc aat aag ccc tcc tct cct cca gaa gaa tta aaa       96
Asp Ser Lys Gly Ser Asn Lys Pro Ser Ser Pro Pro Glu Glu Leu Lys
            20                  25                  30 ttt cag tgt ggc caa aag act ctg agg ccc cgc ttt aag att att ggg      144
Phe Gln Cys Gly Gln Lys Thr Leu Arg Pro Arg Phe Lys Ile Ile Gly
        35                  40                  45 gga gaa ttc acc acc atc gag aac cag ccc tgg ttt gcg gcc atc tac      192
```

```
Gly Glu Phe Thr Thr Ile Glu Asn Gln Pro Trp Phe Ala Ala Ile Tyr
     50                  55                  60 agg agg cac cgg ggg ggc tct gtc acc tac gtg tgt gga ggc agc ctc      240
Arg Arg His Arg Gly Gly Ser Val Thr Tyr Val Cys Gly Gly Ser Leu
 65                  70                  75                  80 atc agc cct tgc tgg gtg atc agc gcc aca cac tgc ttc att gat tac      288
Ile Ser Pro Cys Trp Val Ile Ser Ala Thr His Cys Phe Ile Asp Tyr
                 85                  90                  95 cca aag aag gag gac tac atc gtc tac ctg ggt cgc tca agg ctt aac      336
Pro Lys Lys Glu Asp Tyr Ile Val Tyr Leu Gly Arg Ser Arg Leu Asn
            100                 105                 110 tcc aac acg caa ggg gag atg aag ttt gag gtg gaa aac ctc atc cta      384
Ser Asn Thr Gln Gly Glu Met Lys Phe Glu Val Glu Asn Leu Ile Leu
        115                 120                 125 cac aag gac tac agc gct gac acg ctt gct cac cac aac gac att gcc      432
His Lys Asp Tyr Ser Ala Asp Thr Leu Ala His His Asn Asp Ile Ala
    130                 135                 140 ttg ctg aag atc cgt tcc aag gag ggc agg tgt gcg cag cca tcc cgg      480
Leu Leu Lys Ile Arg Ser Lys Glu Gly Arg Cys Ala Gln Pro Ser Arg
145                 150                 155                 160 act ata cag acc atc tgc ctg ccc tcg atg tat aac gat ccc cag ttt      528
Thr Ile Gln Thr Ile Cys Leu Pro Ser Met Tyr Asn Asp Pro Gln Phe
                165                 170                 175 ggc aca agc tgt gag atc act ggc ttt gga aaa gag aat tct acc gac      576
Gly Thr Ser Cys Glu Ile Thr Gly Phe Gly Lys Glu Asn Ser Thr Asp
            180                 185                 190 tat ctc tat ccg gag cag ctg aaa atg act gtt gtg aag ctg att tcc      624
Tyr Leu Tyr Pro Glu Gln Leu Lys Met Thr Val Val Lys Leu Ile Ser
        195                 200                 205 cac cgg gag tgt cag cag ccc cac tac tac ggc tct gaa gtc acc acc      672
His Arg Glu Cys Gln Gln Pro His Tyr Tyr Gly Ser Glu Val Thr Thr
    210                 215                 220 aaa atg ctg tgt gct gct gac cca cag tgg aaa aca gat tcc tgc cag      720
Lys Met Leu Cys Ala Ala Asp Pro Gln Trp Lys Thr Asp Ser Cys Gln
225                 230                 235                 240 gga gac tca ggg gga ccc ctc gtc tgt tcc ctc caa ggc cgc atg act      768
Gly Asp Ser Gly Gly Pro Leu Val Cys Ser Leu Gln Gly Arg Met Thr
                245                 250                 255 ttg act gga att gtg agc tgg ggc cgt gga tgt gcc ctg aag gac aag      816
Leu Thr Gly Ile Val Ser Trp Gly Arg Gly Cys Ala Leu Lys Asp Lys
            260                 265                 270 cca ggc gtc tac acg aga gtc tca cac ttc tta ccc tgg atc cgc agt      864
Pro Gly Val Tyr Thr Arg Val Ser His Phe Leu Pro Trp Ile Arg Ser
        275                 280                 285 cac acc aag gaa gag aat ggc ctg gcc ctc ttc ccc att cct ctc ccc      912
His Thr Lys Glu Glu Asn Gly Leu Ala Leu Phe Pro Ile Pro Leu Pro
    290                 295                 300 tat tgc tgg ctc tgc agg gct ctg atc aag cgg atc caa gcc atg att      960
Tyr Cys Trp Leu Cys Arg Ala Leu Ile Lys Arg Ile Gln Ala Met Ile
305                 310                 315                 320 ccc aag ggt gcg cta gct gtg gca gtg gcc cag gtg tgc cgc gtg gta     1008
Pro Lys Gly Ala Leu Ala Val Ala Val Ala Gln Val Cys Arg Val Val
                325                 330                 335 cct ctg gtg gcg ggc ggc atc tgc cag tgc ctg gct gag cgc tac tcc     1056
Pro Leu Val Ala Gly Gly Ile Cys Gln Cys Leu Ala Glu Arg Tyr Ser
            340                 345                 350 gtc atc ctg ctc gac acg ctg ctg ggc cgc atg ctg ccc cag ctg gtc     1104
Val Ile Leu Leu Asp Thr Leu Leu Gly Arg Met Leu Pro Gln Leu Val
        355                 360                 365 tgc cgc ctc gtc ctc cgg tgc tcc atg cat cat cat cat cat cat         1149
```

```
Cys Arg Leu Val Leu Arg Cys Ser Met His His His His His
        370                 375                 380

<210> SEQ ID NO 14
<211> LENGTH: 381
<212> TYPE: PRT
<213> ORGANISM: Homo sapiens
<220> FEATURE:
<221> NAME/KEY: DOMAIN
<222> LOCATION: (1)..(381)
<223> OTHER INFORMATION: Surfactant protein B precursor

<400> SEQUENCE: 14

Met Ala Glu Ser His Leu Leu Gln Trp Leu Leu Leu Leu Pro Thr
 1               5                  10                  15

Leu Cys Gly Pro Gly Thr Ala Ala Trp Thr Thr Ser Ser Leu Ala Cys
            20                  25                  30

Ala Gln Gly Pro Glu Phe Trp Cys Gln Ser Leu Glu Gln Ala Leu Gln
        35                  40                  45

Cys Arg Ala Leu Gly His Cys Leu Gln Glu Val Trp Gly His Val Gly
    50                  55                  60

Ala Asp Asp Leu Cys Gln Glu Cys Glu Asp Ile Val His Ile Leu Asn
65                  70                  75                  80

Lys Met Ala Lys Glu Ala Ile Phe Gln Asp Thr Met Arg Lys Phe Leu
                85                  90                  95

Glu Gln Glu Cys Asn Val Leu Pro Leu Lys Leu Leu Met Pro Gln Cys
            100                 105                 110

Asn Gln Val Leu Asp Asp Tyr Phe Pro Leu Val Ile Asp Tyr Phe Gln
        115                 120                 125

Asn Gln Thr Asp Ser Asn Gly Ile Cys Met His Leu Gly Leu Cys Lys
    130                 135                 140

Ser Arg Gln Pro Glu Pro Glu Gln Glu Pro Gly Met Ser Asp Pro Leu
145                 150                 155                 160

Pro Lys Pro Leu Arg Asp Pro Leu Pro Asp Pro Leu Leu Asp Lys Leu
                165                 170                 175

Val Leu Pro Val Leu Pro Gly Ala Leu Gln Ala Arg Pro Gly Pro His
            180                 185                 190

Thr Gln Asp Leu Ser Glu Gln Gln Phe Pro Ile Pro Leu Pro Tyr Cys
        195                 200                 205

Trp Leu Cys Arg Ala Leu Ile Lys Arg Ile Gln Ala Met Ile Pro Lys
    210                 215                 220

Gly Ala Leu Ala Val Ala Val Ala Gln Val Cys Arg Val Val Pro Leu
225                 230                 235                 240

Val Ala Gly Gly Ile Cys Gln Cys Leu Ala Glu Arg Tyr Ser Val Ile
                245                 250                 255

Leu Leu Asp Thr Leu Leu Gly Arg Met Leu Pro Gln Leu Val Cys Arg
            260                 265                 270

Leu Val Leu Arg Cys Ser Met Asp Asp Ser Ala Gly Pro Arg Ser Pro
        275                 280                 285

Thr Gly Glu Trp Leu Pro Arg Asp Ser Glu Cys His Leu Cys Met Ser
    290                 295                 300

Val Thr Thr Gln Ala Gly Asn Ser Ser Glu Gln Ala Ile Pro Gln Ala
305                 310                 315                 320

Met Leu Gln Ala Cys Val Gly Ser Trp Leu Asp Arg Glu Lys Cys Lys
                325                 330                 335

Gln Phe Val Glu Gln His Thr Pro Gln Leu Leu Thr Leu Val Pro Arg
            340                 345                 350
```

```
Gly Trp Asp Ala His Thr Thr Cys Gln Ala Leu Gly Val Cys Gly Thr
        355                 360                 365

Met Ser Ser Pro Leu Gln Cys Ile His Ser Pro Asp Leu
    370                 375                 380

<210> SEQ ID NO 15
<211> LENGTH: 279
<212> TYPE: PRT
<213> ORGANISM: Homo sapiens
<220> FEATURE:
<221> NAME/KEY: DOMAIN
<222> LOCATION: (1)..(279)
<223> OTHER INFORMATION: Surfactant protein B precursor lacking the
      C-terminal propeptide

<400> SEQUENCE: 15

Met Ala Glu Ser His Leu Leu Gln Trp Leu Leu Leu Leu Leu Pro Thr
1               5                   10                  15

Leu Cys Gly Pro Gly Thr Ala Ala Trp Thr Thr Ser Ser Leu Ala Cys
            20                  25                  30

Ala Gln Gly Pro Glu Phe Trp Cys Gln Ser Leu Glu Gln Ala Leu Gln
        35                  40                  45

Cys Arg Ala Leu Gly His Cys Leu Gln Glu Val Trp Gly His Val Gly
    50                  55                  60

Ala Asp Asp Leu Cys Gln Glu Cys Glu Asp Ile Val His Ile Leu Asn
65                  70                  75                  80

Lys Met Ala Lys Glu Ala Ile Phe Gln Asp Thr Met Arg Lys Phe Leu
                85                  90                  95

Glu Gln Glu Cys Asn Val Leu Pro Leu Lys Leu Leu Met Pro Gln Cys
            100                 105                 110

Asn Gln Val Leu Asp Asp Tyr Phe Pro Leu Val Ile Asp Tyr Phe Gln
        115                 120                 125

Asn Gln Thr Asp Ser Asn Gly Ile Cys Met His Leu Gly Leu Cys Lys
    130                 135                 140

Ser Arg Gln Pro Glu Pro Glu Gln Glu Pro Gly Met Ser Asp Pro Leu
145                 150                 155                 160

Pro Lys Pro Leu Arg Asp Pro Leu Pro Asp Pro Leu Leu Asp Lys Leu
                165                 170                 175

Val Leu Pro Val Leu Pro Gly Ala Leu Gln Ala Arg Pro Gly Pro His
            180                 185                 190

Thr Gln Asp Leu Ser Glu Gln Gln Phe Pro Ile Pro Leu Pro Tyr Cys
        195                 200                 205

Trp Leu Cys Arg Ala Leu Ile Lys Arg Ile Gln Ala Met Ile Pro Lys
    210                 215                 220

Gly Ala Leu Ala Val Ala Val Ala Gln Val Cys Arg Val Val Pro Leu
225                 230                 235                 240

Val Ala Gly Gly Ile Cys Gln Cys Leu Ala Glu Arg Tyr Ser Val Ile
                245                 250                 255

Leu Leu Asp Thr Leu Leu Gly Arg Met Leu Pro Gln Leu Val Cys Arg
            260                 265                 270

Leu Val Leu Arg Cys Ser Met
        275

<210> SEQ ID NO 16
<211> LENGTH: 79
<212> TYPE: PRT
<213> ORGANISM: Homo sapiens
<220> FEATURE:
```

```
<221> NAME/KEY: DOMAIN
<222> LOCATION: (1)..(79)
<223> OTHER INFORMATION: Mature surfactant protein B

<400> SEQUENCE: 16

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
                20                  25                  30

Gln Val Cys Arg Val Val Pro Leu Val Ala Gly Gly Ile Cys Gln Cys
            35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys Ser Met
65                  70                  75

<210> SEQ ID NO 17
<211> LENGTH: 431
<212> TYPE: PRT
<213> ORGANISM: Homo sapiens
<220> FEATURE:
<221> NAME/KEY: DOMAIN
<222> LOCATION: (1)..(431)
<223> OTHER INFORMATION: Single-chain urokinase-plasminogen activator

<400> SEQUENCE: 17

Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
                20                  25                  30

Cys Leu Asn Gly Gly Thr Cys Val Ser Asn Lys Tyr Phe Ser Asn Ile
            35                  40                  45

His Trp Cys Asn Cys Pro Lys Lys Phe Gly Gly Gln His Cys Glu Ile
    50                  55                  60

Asp Lys Ser Lys Thr Cys Tyr Glu Gly Asn Gly His Phe Tyr Arg Gly
65                  70                  75                  80

Lys Ala Ser Thr Asp Thr Met Gly Arg Pro Cys Leu Pro Trp Asn Ser
                85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
    115                 120                 125

Arg Arg Pro Trp Cys Tyr Val Gln Val Gly Leu Lys Pro Leu Val Gln
130                 135                 140

Glu Cys Met Val His Asp Cys Ala Asp Gly Lys Lys Pro Ser Ser Pro
145                 150                 155                 160

Pro Glu Glu Leu Lys Phe Gln Cys Gly Gln Lys Thr Leu Arg Pro Arg
                165                 170                 175

Phe Lys Ile Ile Gly Gly Glu Phe Thr Thr Ile Glu Asn Gln Pro Trp
            180                 185                 190

Phe Ala Ala Ile Tyr Arg Arg His Arg Gly Gly Ser Val Thr Tyr Val
    195                 200                 205

Cys Gly Gly Ser Leu Ile Ser Pro Cys Trp Val Ile Ser Ala Thr His
210                 215                 220

Cys Phe Ile Asp Tyr Pro Lys Lys Glu Asp Tyr Ile Val Tyr Leu Gly
225                 230                 235                 240

Arg Ser Arg Leu Asn Ser Asn Thr Gln Gly Glu Met Lys Phe Glu Val
                245                 250                 255
```

```
Glu Asn Leu Ile Leu His Lys Asp Tyr Ser Ala Asp Thr Leu Ala His
            260                 265                 270

His Asn Asp Ile Ala Leu Leu Lys Ile Arg Ser Lys Glu Gly Arg Cys
        275                 280                 285

Ala Gln Pro Ser Arg Thr Ile Gln Thr Ile Cys Leu Pro Ser Met Tyr
    290                 295                 300

Asn Asp Pro Gln Phe Gly Thr Ser Cys Glu Ile Thr Gly Phe Gly Lys
305                 310                 315                 320

Glu Asn Ser Thr Asp Tyr Leu Tyr Pro Glu Gln Leu Lys Met Thr Val
                325                 330                 335

Val Lys Leu Ile Ser His Arg Glu Cys Gln Gln Pro His Tyr Tyr Gly
            340                 345                 350

Ser Glu Val Thr Thr Lys Met Leu Cys Ala Ala Asp Pro Gln Trp Lys
        355                 360                 365

Thr Asp Ser Cys Gln Gly Asp Ser Gly Gly Pro Leu Val Cys Ser Leu
    370                 375                 380

Gln Gly Arg Met Thr Leu Thr Gly Ile Val Ser Trp Gly Arg Gly Cys
385                 390                 395                 400

Ala Leu Lys Asp Lys Pro Gly Val Tyr Thr Arg Val Ser His Phe Leu
                405                 410                 415

Pro Trp Ile Arg Ser His Thr Lys Glu Glu Asn Gly Leu Ala Leu
            420                 425                 430

<210> SEQ ID NO 18
<211> LENGTH: 276
<212> TYPE: PRT
<213> ORGANISM: Homo sapiens
<220> FEATURE:
<221> NAME/KEY: DOMAIN
<222> LOCATION: (1)..(276)
<223> OTHER INFORMATION: Low molecular weight two-chain
      urokinase-plasminogen activator

<400> SEQUENCE: 18

Lys Pro Ser Ser Pro Glu Glu Leu Lys Phe Gln Cys Gly Gln Lys
1               5                   10                  15

Thr Leu Arg Pro Arg Phe Lys Ile Ile Gly Gly Glu Phe Thr Thr Ile
            20                  25                  30

Glu Asn Gln Pro Trp Phe Ala Ala Ile Tyr Arg Arg His Arg Gly Gly
        35                  40                  45

Ser Val Thr Tyr Val Cys Gly Gly Ser Leu Ile Ser Pro Cys Trp Val
    50                  55                  60

Ile Ser Ala Thr His Cys Phe Ile Asp Tyr Pro Lys Lys Glu Asp Tyr
65                  70                  75                  80

Ile Val Tyr Leu Gly Arg Ser Arg Leu Asn Ser Asn Thr Gln Gly Glu
                85                  90                  95

Met Lys Phe Glu Val Glu Asn Leu Ile Leu His Lys Asp Tyr Ser Ala
            100                 105                 110

Asp Thr Leu Ala His His Asn Asp Ile Ala Leu Leu Lys Ile Arg Ser
        115                 120                 125

Lys Glu Gly Arg Cys Ala Gln Pro Ser Arg Thr Ile Gln Thr Ile Cys
    130                 135                 140

Leu Pro Ser Met Tyr Asn Asp Pro Gln Phe Gly Thr Ser Cys Glu Ile
145                 150                 155                 160

Thr Gly Phe Gly Lys Glu Asn Ser Thr Asp Tyr Leu Tyr Pro Glu Gln
                165                 170                 175
```

```
Leu Lys Met Thr Val Lys Leu Ile Ser His Arg Glu Cys Gln Gln
            180                 185                 190

Pro His Tyr Tyr Gly Ser Glu Val Thr Thr Lys Met Leu Cys Ala Ala
        195                 200                 205

Asp Pro Gln Trp Lys Thr Asp Ser Cys Gln Gly Asp Ser Gly Gly Pro
    210                 215                 220

Leu Val Cys Ser Leu Gln Gly Arg Met Thr Leu Thr Gly Ile Val Ser
225                 230                 235                 240

Trp Gly Arg Gly Cys Ala Leu Lys Asp Lys Pro Gly Val Tyr Thr Arg
                245                 250                 255

Val Ser His Phe Leu Pro Trp Ile Arg Ser His Thr Lys Glu Glu Asn
            260                 265                 270

Gly Leu Ala Leu
        275

<210> SEQ ID NO 19
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DOMAIN
<222> LOCATION: (1)..(279)
<223> OTHER INFORMATION: Human surfactant protein B precursor lacking
      the C-terminal propeptide
<220> FEATURE:
<221> NAME/KEY: DOMAIN
<222> LOCATION: (280)..(281)
<223> OTHER INFORMATION: Linker
<220> FEATURE:
<221> NAME/KEY: DOMAIN
<222> LOCATION: (282)..(557)
<223> OTHER INFORMATION: Human low molecular weight two-chain
      urokinase-plasminogen activator

<400> SEQUENCE: 19

Met Ala Glu Ser His Leu Leu Gln Trp Leu Leu Leu Leu Pro Thr
1               5                   10                  15

Leu Cys Gly Pro Gly Thr Ala Ala Trp Thr Thr Ser Ser Leu Ala Cys
            20                  25                  30

Ala Gln Gly Pro Glu Phe Trp Cys Gln Ser Leu Glu Gln Ala Leu Gln
        35                  40                  45

Cys Arg Ala Leu Gly His Cys Leu Gln Glu Val Trp Gly His Val Gly
    50                  55                  60

Ala Asp Asp Leu Cys Gln Glu Cys Glu Asp Ile Val His Ile Leu Asn
65                  70                  75                  80

Lys Met Ala Lys Glu Ala Ile Phe Gln Asp Thr Met Arg Lys Phe Leu
                85                  90                  95

Glu Gln Glu Cys Asn Val Leu Pro Leu Lys Leu Leu Met Pro Gln Cys
            100                 105                 110

Asn Gln Val Leu Asp Asp Tyr Phe Pro Leu Val Ile Asp Tyr Phe Gln
        115                 120                 125

Asn Gln Thr Asp Ser Asn Gly Ile Cys Met His Leu Gly Leu Cys Lys
    130                 135                 140

Ser Arg Gln Pro Glu Pro Glu Gln Glu Pro Gly Met Ser Asp Pro Leu
145                 150                 155                 160

Pro Lys Pro Leu Arg Asp Pro Leu Pro Asp Pro Leu Leu Asp Lys Leu
                165                 170                 175

Val Leu Pro Val Leu Pro Gly Ala Leu Gln Ala Arg Pro Gly Pro His
```

```
                180                 185                 190
Thr Gln Asp Leu Ser Glu Gln Gln Phe Pro Ile Pro Leu Pro Tyr Cys
            195                 200                 205

Trp Leu Cys Arg Ala Leu Ile Lys Arg Ile Gln Ala Met Ile Pro Lys
        210                 215                 220

Gly Ala Leu Ala Val Ala Val Ala Gln Val Cys Arg Val Val Pro Leu
225                 230                 235                 240

Val Ala Gly Gly Ile Cys Gln Cys Leu Ala Glu Arg Tyr Ser Val Ile
                245                 250                 255

Leu Leu Asp Thr Leu Leu Gly Arg Met Leu Pro Gln Leu Val Cys Arg
            260                 265                 270

Leu Val Leu Arg Cys Ser Met Lys Leu Lys Pro Ser Pro Pro Glu
        275                 280                 285

Glu Leu Lys Phe Gln Cys Gly Gln Lys Thr Leu Arg Pro Arg Phe Lys
        290                 295                 300

Ile Ile Gly Gly Glu Phe Thr Thr Ile Glu Asn Gln Pro Trp Phe Ala
305                 310                 315                 320

Ala Ile Tyr Arg Arg His Arg Gly Gly Ser Val Thr Tyr Val Cys Gly
                325                 330                 335

Gly Ser Leu Ile Ser Pro Cys Trp Val Ile Ser Ala Thr His Cys Phe
            340                 345                 350

Ile Asp Tyr Pro Lys Lys Glu Asp Tyr Ile Val Tyr Leu Gly Arg Ser
        355                 360                 365

Arg Leu Asn Ser Asn Thr Gln Gly Glu Met Lys Phe Glu Val Glu Asn
        370                 375                 380

Leu Ile Leu His Lys Asp Tyr Ser Ala Asp Thr Leu Ala His His Asn
385                 390                 395                 400

Asp Ile Ala Leu Leu Lys Ile Arg Ser Lys Glu Gly Arg Cys Ala Gln
                405                 410                 415

Pro Ser Arg Thr Ile Gln Thr Ile Cys Leu Pro Ser Met Tyr Asn Asp
            420                 425                 430

Pro Gln Phe Gly Thr Ser Cys Glu Ile Thr Gly Phe Gly Lys Glu Asn
        435                 440                 445

Ser Thr Asp Tyr Leu Tyr Pro Glu Gln Leu Lys Met Thr Val Val Lys
        450                 455                 460

Leu Ile Ser His Arg Glu Cys Gln Gln Pro His Tyr Tyr Gly Ser Glu
465                 470                 475                 480

Val Thr Thr Lys Met Leu Cys Ala Ala Asp Pro Gln Trp Lys Thr Asp
                485                 490                 495

Ser Cys Gln Gly Asp Ser Gly Gly Pro Leu Val Cys Ser Leu Gln Gly
            500                 505                 510

Arg Met Thr Leu Thr Gly Ile Val Ser Trp Gly Arg Gly Cys Ala Leu
        515                 520                 525

Lys Asp Lys Pro Gly Val Tyr Thr Arg Val Ser His Phe Leu Pro Trp
        530                 535                 540

Ile Arg Ser His Thr Lys Glu Glu Asn Gly Leu Ala Leu
545                 550                 555

<210> SEQ ID NO 20
<211> LENGTH: 558
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: DOMAIN
<222> LOCATION: (1)..(279)
<223> OTHER INFORMATION: Human surfactant protein B precursor lacking
      the C-terminal propeptide
<220> FEATURE:
<221> NAME/KEY: DOMAIN
<222> LOCATION: (280)..(282)
<223> OTHER INFORMATION: Linker
<220> FEATURE:
<221> NAME/KEY: DOMAIN
<222> LOCATION: (283)..(558)
<223> OTHER INFORMATION: Human low molecular weight two-chain
      urokinase-plasminogen activator

<400> SEQUENCE: 20
```

Met Ala Glu Ser His Leu Leu Gln Trp Leu Leu Leu Leu Pro Thr
1               5                   10                  15

Leu Cys Gly Pro Gly Thr Ala Ala Trp Thr Thr Ser Ser Leu Ala Cys
            20                  25                  30

Ala Gln Gly Pro Glu Phe Trp Cys Gln Ser Leu Glu Gln Ala Leu Gln
            35                  40                  45

Cys Arg Ala Leu Gly His Cys Leu Gln Glu Val Trp Gly His Val Gly
50                  55                  60

Ala Asp Asp Leu Cys Gln Cys Glu Asp Ile Val His Ile Leu Asn
65                  70                  75                  80

Lys Met Ala Lys Glu Ala Ile Phe Gln Asp Thr Met Arg Lys Phe Leu
                85                  90                  95

Glu Gln Glu Cys Asn Val Leu Pro Leu Lys Leu Leu Met Pro Gln Cys
            100                 105                 110

Asn Gln Val Leu Asp Asp Tyr Phe Pro Leu Val Ile Asp Tyr Phe Gln
            115                 120                 125

Asn Gln Thr Asp Ser Asn Gly Ile Cys Met His Leu Gly Leu Cys Lys
    130                 135                 140

Ser Arg Gln Pro Glu Pro Glu Gln Glu Pro Gly Met Ser Asp Pro Leu
145                 150                 155                 160

Pro Lys Pro Leu Arg Asp Pro Leu Pro Asp Pro Leu Leu Asp Lys Leu
                165                 170                 175

Val Leu Pro Val Leu Pro Gly Ala Leu Gln Ala Arg Pro Gly Pro His
            180                 185                 190

Thr Gln Asp Leu Ser Glu Gln Gln Phe Pro Ile Pro Leu Pro Tyr Cys
            195                 200                 205

Trp Leu Cys Arg Ala Leu Ile Lys Arg Ile Gln Ala Met Ile Pro Lys
    210                 215                 220

Gly Ala Leu Ala Val Ala Val Ala Gln Val Cys Arg Val Val Pro Leu
225                 230                 235                 240

Val Ala Gly Gly Ile Cys Gln Cys Leu Ala Glu Arg Tyr Ser Val Ile
                245                 250                 255

Leu Leu Asp Thr Leu Leu Gly Arg Met Leu Pro Gln Leu Val Cys Arg
            260                 265                 270

Leu Val Leu Arg Cys Ser Met Gln Ile Ser Lys Pro Ser Pro Pro
            275                 280                 285

Glu Glu Leu Lys Phe Gln Cys Gly Gln Lys Thr Leu Arg Pro Arg Phe
    290                 295                 300

Lys Ile Ile Gly Gly Glu Phe Thr Thr Ile Glu Asn Gln Pro Trp Phe
305                 310                 315                 320

Ala Ala Ile Tyr Arg Arg His Arg Gly Gly Ser Val Thr Tyr Val Cys
                325                 330                 335

Gly Gly Ser Leu Ile Ser Pro Cys Trp Val Ile Ser Ala Thr His Cys

-continued

```
                340             345             350
Phe Ile Asp Tyr Pro Lys Lys Glu Asp Tyr Ile Val Tyr Leu Gly Arg
            355                 360                 365
Ser Arg Leu Asn Ser Asn Thr Gln Gly Glu Met Lys Phe Glu Val Glu
        370                 375                 380
Asn Leu Ile Leu His Lys Asp Tyr Ser Ala Asp Thr Leu Ala His His
385                 390                 395                 400
Asn Asp Ile Ala Leu Leu Lys Ile Arg Ser Lys Glu Gly Arg Cys Ala
                405                 410                 415
Gln Pro Ser Arg Thr Ile Gln Thr Ile Cys Leu Pro Ser Met Tyr Asn
            420                 425                 430
Asp Pro Gln Phe Gly Thr Ser Cys Glu Ile Thr Gly Phe Gly Lys Glu
        435                 440                 445
Asn Ser Thr Asp Tyr Leu Tyr Pro Glu Gln Leu Lys Met Thr Val Val
    450                 455                 460
Lys Leu Ile Ser His Arg Glu Cys Gln Gln Pro His Tyr Tyr Gly Ser
465                 470                 475                 480
Glu Val Thr Thr Lys Met Leu Cys Ala Ala Asp Pro Gln Trp Lys Thr
                485                 490                 495
Asp Ser Cys Gln Gly Asp Ser Gly Gly Pro Leu Val Cys Ser Leu Gln
            500                 505                 510
Gly Arg Met Thr Leu Thr Gly Ile Val Ser Trp Gly Arg Gly Cys Ala
        515                 520                 525
Leu Lys Asp Lys Pro Gly Val Tyr Thr Arg Val Ser His Phe Leu Pro
    530                 535                 540
Trp Ile Arg Ser His Thr Lys Glu Gln Asn Gly Leu Ala Leu
545                 550                 555
```

<210> SEQ ID NO 21
<211> LENGTH: 197
<212> TYPE: PRT
<213> ORGANISM: Homo sapiens
<220> FEATURE:
<221> NAME/KEY: DOMAIN
<222> LOCATION: (1)..(197)
<223> OTHER INFORMATION: Surfactant protein C precursor

<400> SEQUENCE: 21

```
Met Asp Val Gly Ser Lys Glu Val Leu Met Glu Ser Pro Pro Asp Tyr
1               5                   10                  15
Ser Ala Ala Pro Arg Gly Arg Phe Gly Ile Pro Cys Cys Pro Val His
            20                  25                  30
Leu Lys Arg Leu Leu Ile Val Val Val Val Val Leu Ile Val Val
        35                  40                  45
Val Ile Val Gly Ala Leu Leu Met Gly Leu His Met Ser Gln Lys His
    50                  55                  60
Thr Glu Met Val Leu Glu Met Ser Ile Gly Ala Pro Glu Ala Gln Gln
65                  70                  75                  80
Arg Leu Ala Leu Ser Glu His Leu Val Thr Thr Ala Thr Phe Ser Ile
                85                  90                  95
Gly Ser Thr Gly Leu Val Val Tyr Asp Tyr Gln Gln Leu Leu Ile Ala
            100                 105                 110
Tyr Lys Pro Ala Pro Gly Thr Cys Cys Tyr Ile Met Lys Ile Ala Pro
        115                 120                 125
Glu Ser Ile Pro Ser Leu Glu Ala Leu Thr Arg Lys Val His Asn Phe
    130                 135                 140
```

```
Gln Met Glu Cys Ser Leu Gln Ala Lys Pro Ala Val Pro Thr Ser Lys
145                 150                 155                 160

Leu Gly Gln Ala Glu Gly Arg Asp Ala Gly Ser Ala Pro Ser Gly Gly
                165                 170                 175

Asp Pro Ala Phe Leu Gly Met Ala Val Ser Thr Leu Cys Gly Glu Val
            180                 185                 190

Pro Leu Tyr Tyr Ile
        195

<210> SEQ ID NO 22
<211> LENGTH: 58
<212> TYPE: PRT
<213> ORGANISM: Homo sapiens
<220> FEATURE:
<221> NAME/KEY: DOMAIN
<222> LOCATION: (1)..(58)
<223> OTHER INFORMATION: Surfactant protein C precursor lacking the
      C-terminal propeptide

<400> SEQUENCE: 22

Met Asp Val Gly Ser Lys Glu Val Leu Met Glu Ser Pro Pro Asp Tyr
1               5                   10                  15

Ser Ala Ala Pro Arg Gly Arg Phe Gly Ile Pro Cys Cys Pro Val His
                20                  25                  30

Leu Lys Arg Leu Leu Ile Val Val Val Val Val Leu Ile Val Val
            35                  40                  45

Val Ile Val Gly Ala Leu Leu Met Gly Leu
        50                  55

<210> SEQ ID NO 23
<211> LENGTH: 35
<212> TYPE: PRT
<213> ORGANISM: Homo sapiens
<220> FEATURE:
<221> NAME/KEY: DOMAIN
<222> LOCATION: (1)..(35)
<223> OTHER INFORMATION: Mature surfactant protein C

<400> SEQUENCE: 23

Phe Gly Ile Pro Cys Cys Pro Val His Leu Lys Arg Leu Leu Ile Val
1               5                   10                  15

Val Val Val Val Val Leu Ile Val Val Val Ile Val Gly Ala Leu Leu
                20                  25                  30

Met Gly Leu
        35

<210> SEQ ID NO 24
<211> LENGTH: 562
<212> TYPE: PRT
<213> ORGANISM: Homo sapiens
<220> FEATURE:
<221> NAME/KEY: DOMAIN
<222> LOCATION: (1)..(562)
<223> OTHER INFORMATION: Tissue-plasminogen activator

<400> SEQUENCE: 24

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ser Tyr Gln Val Ile Cys Arg Asp Glu Lys Thr Gln Met
            35                  40                  45

Ile Tyr Gln Gln His Gln Ser Trp Leu Arg Pro Val Leu Arg Ser Asn
```

-continued

```
            50                  55                  60
Arg Val Glu Tyr Cys Trp Cys Asn Ser Gly Arg Ala Gln Cys His Ser
 65                  70                  75                  80

Val Pro Val Lys Ser Cys Ser Glu Pro Arg Cys Phe Asn Gly Gly Thr
                 85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
            115                 120                 125

Glu Asp Gln Gly Ile Ser Tyr Arg Gly Thr Trp Ser Thr Ala Glu Ser
130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
                180                 185                 190

Phe Lys Ala Gly Lys Tyr Ser Ser Glu Phe Cys Ser Thr Pro Ala Cys
            195                 200                 205

Ser Glu Gly Asn Ser Asp Cys Tyr Phe Gly Asn Gly Ser Ala Tyr Arg
210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
            275                 280                 285

Glu Tyr Cys Asp Val Pro Ser Cys Ser Thr Cys Gly Leu Arg Gln Tyr
290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
            340                 345                 350

Leu Ser Ala Ala His Cys Phe Gln Glu Arg Phe Pro Pro His His Leu
            355                 360                 365

Thr Val Ile Leu Gly Arg Thr Tyr Arg Val Val Pro Gly Glu Glu Glu
370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
            420                 425                 430

Pro Ala Asp Leu Gln Leu Pro Asp Trp Thr Glu Cys Glu Leu Ser Gly
            435                 440                 445

Tyr Gly Lys His Glu Ala Leu Ser Pro Phe Tyr Ser Glu Arg Leu Lys
            450                 455                 460

Glu Ala His Val Arg Leu Tyr Pro Ser Ser Arg Cys Thr Ser Gln His
465                 470                 475                 480
```

-continued

```
Leu Leu Asn Arg Thr Val Thr Asp Asn Met Leu Cys Ala Gly Asp Thr
            485                 490                 495

Arg Ser Gly Gly Pro Gln Ala Asn Leu His Asp Ala Cys Gln Gly Asp
        500                 505                 510

Ser Gly Gly Pro Leu Val Cys Leu Asn Asp Gly Arg Met Thr Leu Val
        515                 520                 525

Gly Ile Ile Ser Trp Gly Leu Gly Cys Gly Gln Lys Asp Val Pro Gly
        530                 535                 540

Val Tyr Thr Lys Val Thr Asn Tyr Leu Asp Trp Ile Arg Asp Asn Met
545                 550                 555                 560

Arg Pro

<210> SEQ ID NO 25
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DOMAIN
<222> LOCATION: (1)..(23)
<223> OTHER INFORMATION: Signal sequence of the surfactant protein B
<220> FEATURE:
<221> NAME/KEY: DOMAIN
<222> LOCATION: (24)..(25)
<223> OTHER INFORMATION: Linker
<220> FEATURE:
<221> NAME/KEY: DOMAIN
<222> LOCATION: (26)..(104)
<223> OTHER INFORMATION: Mature surfactant protein B
<220> FEATURE:
<221> NAME/KEY: DOMAIN
<222> LOCATION: (105)..(380)
<223> OTHER INFORMATION: Human low molecular weight two-chain
      urokinase-plasminogen activator
<220> FEATURE:
<221> NAME/KEY: DOMAIN
<222> LOCATION: (381)..(386)
<223> OTHER INFORMATION: Hexahistidine affinity tag

<400> SEQUENCE: 25

Met Ala Glu Ser His Leu Leu Gln Trp Leu Leu Leu Leu Leu Pro Thr
1               5                   10                  15

Leu Cys Gly Pro Gly Thr Ala Ala Trp Phe Pro Ile Pro Leu Pro Tyr
                20                  25                  30

Cys Trp Leu Cys Arg Ala Leu Ile Lys Arg Ile Gln Ala Met Ile Pro
            35                  40                  45

Lys Gly Ala Leu Ala Val Ala Val Ala Gln Val Cys Arg Val Val Pro
        50                  55                  60

Leu Val Ala Gly Gly Ile Cys Gln Cys Leu Ala Glu Arg Tyr Ser Val
65                  70                  75                  80

Ile Leu Leu Asp Thr Leu Leu Gly Arg Met Leu Pro Gln Leu Val Cys
                85                  90                  95

Arg Leu Val Leu Arg Cys Ser Met Lys Pro Ser Ser Pro Pro Glu Glu
            100                 105                 110

Leu Lys Phe Gln Cys Gly Gln Lys Thr Leu Arg Pro Arg Phe Lys Ile
        115                 120                 125

Ile Gly Gly Glu Phe Thr Thr Ile Glu Asn Gln Pro Trp Phe Ala Ala
        130                 135                 140

Ile Tyr Arg Arg His Arg Gly Gly Ser Val Thr Tyr Val Cys Gly Gly
145                 150                 155                 160

Ser Leu Ile Ser Pro Cys Trp Val Ile Ser Ala Thr His Cys Phe Ile
```

```
                    165                 170                 175
Asp Tyr Pro Lys Lys Glu Asp Tyr Ile Val Tyr Leu Gly Arg Ser Arg
            180                 185                 190

Leu Asn Ser Asn Thr Gln Gly Glu Met Lys Phe Glu Val Glu Asn Leu
        195                 200                 205

Ile Leu His Lys Asp Tyr Ser Ala Asp Thr Leu Ala His His Asn Asp
    210                 215                 220

Ile Ala Leu Leu Lys Ile Arg Ser Lys Glu Gly Arg Cys Ala Gln Pro
225                 230                 235                 240

Ser Arg Thr Ile Gln Thr Ile Cys Leu Pro Ser Met Tyr Asn Asp Pro
                245                 250                 255

Gln Phe Gly Thr Ser Cys Glu Ile Thr Gly Phe Gly Lys Glu Asn Ser
            260                 265                 270

Thr Asp Tyr Leu Tyr Pro Glu Gln Leu Lys Met Thr Val Val Lys Leu
        275                 280                 285

Ile Ser His Arg Glu Cys Gln Gln Pro His Tyr Tyr Gly Ser Glu Val
    290                 295                 300

Thr Thr Lys Met Leu Cys Ala Ala Asp Pro Gln Trp Lys Thr Asp Ser
305                 310                 315                 320

Cys Gln Gly Asp Ser Gly Gly Pro Leu Val Cys Ser Leu Gln Gly Arg
                325                 330                 335

Met Thr Leu Thr Gly Ile Val Ser Trp Gly Arg Gly Cys Ala Leu Lys
            340                 345                 350

Asp Lys Pro Gly Val Tyr Thr Arg Val Ser His Phe Leu Pro Trp Ile
        355                 360                 365

Arg Ser His Thr Lys Glu Glu Asn Gly Leu Ala Leu His His His His
    370                 375                 380

His His
385

<210> SEQ ID NO 26
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DOMAIN
<222> LOCATION: (1)..(20)
<223> OTHER INFORMATION: Signal sequence of the urokinase plasminogen
      activator
<220> FEATURE:
<221> NAME/KEY: DOMAIN
<222> LOCATION: (21)..(22)
<223> OTHER INFORMATION: Linker
<220> FEATURE:
<221> NAME/KEY: DOMAIN
<222> LOCATION: (23)..(298)
<223> OTHER INFORMATION: Human low molecular weight two chain
      urokinase-plasminogen activator
<220> FEATURE:
<221> NAME/KEY: DOMAIN
<222> LOCATION: (299)..(377)
<223> OTHER INFORMATION: Mature surfactant protein B
<220> FEATURE:
<221> NAME/KEY: CDS
<222> LOCATION: (378)..(383)
<223> OTHER INFORMATION: Hexahistidine affinity tag

<400> SEQUENCE: 26

Met Arg Ala Leu Leu Ala Arg Leu Leu Leu Cys Val Leu Val Val Ser
1               5                   10                  15
```

-continued

```
Asp Ser Lys Gly Ser Asn Lys Pro Ser Pro Glu Glu Leu Lys
         20                  25                  30

Phe Gln Cys Gly Gln Lys Thr Leu Arg Pro Arg Phe Lys Ile Ile Gly
         35                  40                  45

Gly Glu Phe Thr Thr Ile Glu Asn Gln Pro Trp Phe Ala Ala Ile Tyr
 50                  55                  60

Arg Arg His Arg Gly Gly Ser Val Thr Tyr Val Cys Gly Gly Ser Leu
 65                  70                  75                  80

Ile Ser Pro Cys Trp Val Ile Ser Ala Thr His Cys Phe Ile Asp Tyr
                 85                  90                  95

Pro Lys Lys Glu Asp Tyr Ile Val Tyr Leu Gly Arg Ser Arg Leu Asn
            100                 105                 110

Ser Asn Thr Gln Gly Glu Met Lys Phe Glu Val Glu Asn Leu Ile Leu
        115                 120                 125

His Lys Asp Tyr Ser Ala Asp Thr Leu Ala His His Asn Asp Ile Ala
    130                 135                 140

Leu Leu Lys Ile Arg Ser Lys Glu Gly Arg Cys Ala Gln Pro Ser Arg
145                 150                 155                 160

Thr Ile Gln Thr Ile Cys Leu Pro Ser Met Tyr Asn Asp Pro Gln Phe
                165                 170                 175

Gly Thr Ser Cys Glu Ile Thr Gly Phe Gly Lys Glu Asn Ser Thr Asp
            180                 185                 190

Tyr Leu Tyr Pro Glu Gln Leu Lys Met Thr Val Val Lys Leu Ile Ser
        195                 200                 205

His Arg Glu Cys Gln Gln Pro His Tyr Tyr Gly Ser Glu Val Thr Thr
    210                 215                 220

Lys Met Leu Cys Ala Ala Asp Pro Gln Trp Lys Thr Asp Ser Cys Gln
225                 230                 235                 240

Gly Asp Ser Gly Gly Pro Leu Val Cys Ser Leu Gln Gly Arg Met Thr
                245                 250                 255

Leu Thr Gly Ile Val Ser Trp Gly Arg Gly Cys Ala Leu Lys Asp Lys
            260                 265                 270

Pro Gly Val Tyr Thr Arg Val Ser His Phe Leu Pro Trp Ile Arg Ser
        275                 280                 285

His Thr Lys Glu Glu Asn Gly Leu Ala Leu Phe Pro Ile Pro Leu Pro
    290                 295                 300

Tyr Cys Trp Leu Cys Arg Ala Leu Ile Lys Arg Ile Gln Ala Met Ile
305                 310                 315                 320

Pro Lys Gly Ala Leu Ala Val Ala Val Ala Gln Val Cys Arg Val Val
                325                 330                 335

Pro Leu Val Ala Gly Gly Ile Cys Gln Cys Leu Ala Glu Arg Tyr Ser
            340                 345                 350

Val Ile Leu Leu Asp Thr Leu Leu Gly Arg Met Leu Pro Gln Leu Val
        355                 360                 365

Cys Arg Leu Val Leu Arg Cys Ser Met His His His His
    370                 375                 380
```

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 27

His His His His His His
1               5

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctcgagatgg ctgag                                                    15

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgctccatga agcttaagcc ctcc                                          24

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtcgccctca tccttaag                                                 18

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggcgcgccat ggct                                                     14

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tccatgcaga tatctaagcc c                                             21

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gccctcgctc ga                                                       12

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tctagagcca ccatggct                                                    18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
actgctgcct ggttcccc                                                    18

<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tccatgaagc cc                                                          12

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cattagtaag cggccgcc                                                    18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tctagagcca ccatgaga                                                    18

<210> SEQ ID NO 39
<211> LENGTH: 18
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 39
aaaggcagca ataagccc                                                    18

<210> SEQ ID NO 40
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gccctcttcc cc                                                          12
```

CHIMERIC PLASMINOGEN ACTIVATORS AND THEIR PHARMACEUTICAL USE

This Application is a U.S. national stage filing under 35 U.S.C. 371 of PCT/EP2003/014542 filed Dec. 18, 2003, from which priority is claimed.

The present invention relates to recombinant chimeric proteins comprising a surfactant protein precursor N-terminally fused to a plasminogen activator or comprising a mature surfactant protein N-terminally or C-terminally fused to a plasminogen activator. The invention is also directed to the corresponding nucleic acid molecules encoding such fusion proteins as well as to a method for their production. The invention further refers to a pharmaceutical composition comprising such a fusion protein and to pharmacological uses of an inventive fusion protein for the prevention and/or treatment of inflammatory and interstitial lung diseases.

Numerous acute inflammatory and chronic interstitial lung diseases, such as the acute respiratory distress syndrome (ARDS), acute lung injury (ALI), interstitial lung disease (GM) or idiopathic pulmonary fibrosis (IPF), are characterized by substantial surfactant abnormalities, e.g. alterations in surfactant composition, leakage of plasma proteins into the alveolar space, or intra-alveolar accumulation of fibrin (reviewed in [1,2]).

Under these pathological conditions, the alveolar hemostatic balance is shifted towards a predominance of pro-coagulant and anti-fibrinolytic activities, whereas the fibrinolytic activity of the alveolar space is markedly reduced, with depressed levels of urokinase-plasminogen activator (u-PA; also termed urokinase), the predominant plasminogen activator in this compartment, but elevated concentrations of plasminogen activator inhibitor 1 (PAI-1) and $\alpha_2$-antiplasmin [3-5]. In such a setting, fibrinogen leaking into the alveolar space due to an impaired function of the air/blood-barrier (consisting of the capillary endothelium, the interstitial space, and the alveolar epithelium) is rapidly converted into fibrin, and alveolar fibrin accumulation is observed.

The function of fibrin formation in the alveolar space is largely unknown. It may have beneficial effects in preventing pulmonary hemorrhage and serve as primary matrix of wound repair. On the other hand, alveolar fibrin may contribute to the impairment of gas exchange in acute lung injury, and a delayed clearance of alveolar fibrin may provide a provisional matrix for subsequent fibroblast invasion as well as production of extra-cellular matrix proteins and thus promote the fibroproliferative response that characterizes a prolonged course of ARDS and lung fibrosis (reviewed in [6-8]).

Pulmonary surfactant is a lipoprotein complex covering the alveolar surface of all mammalian lungs (reviewed in [9, 10]). By reducing the surface tension at the air/liquid-interface to very low levels, it makes alveolar ventilation and gas exchange feasible at low physiologic pulmonary pressures and prevents alveoli from collapsing. Pulmonary surfactant is composed of approximately 90% lipids and 10% proteins. Of the lipids, 80-90% are phospholipids, with phosphatidylcholine as the most abundant component. To date, four surfactant-associated proteins have been identified which can be divided into two groups: the hydrophilic surfactant proteins (SP) SP-A and SP-D, and the hydrophobic surfactant proteins SP-B and SP-C (reviewed in [11, 12]).

In recent years, application of exogenous surfactant preparations has become an interesting approach to restore surfactant dysfunction in pathological conditions, such as ARDS or IRDS. For example, the International PCT Application [13] discloses a pharmaceutical preparation for treating infant respiratory distress syndrome or acute lung injury, comprising at least one modification of SP-B and at least one modification of SP-C. The authors have found that by adding modifications of SP-C to pulmonary surfactant preparations containing modifications of SP-B, pharmaceutical preparations with advantageous properties are obtained. The modifications of the surfactant proteins may be recombinant proteins. U.S. Patent [14] describes a composition for pulmonary administration of a pharmaceutically active compound comprising a liposome forming compound as well as at least one alveolar surfactant protein in an amount effective to enhance transport of the liposomes across a pulmonary surface. Finally, U.S. Patent [15] describes several fragments of SP-B that exhibit surfactant activity when admixed with phospholipids. These fragments are suitable compounds for the preparation of therapeutically effective formulations for the treatment of respiratory disease.

Surfactant abnormalities are assumed to represent key events in the development of acute and chronic respiratory failure. Impairment of biophysical surfactant function with increased minimum surface tension and altered phospholipid- and surfactant protein-profiles have consistently been observed in patients with ARDS, severe pneumonia as well as interstitial lung disease (reviewed in [1,2]). Furthermore, it has been established that alveolar fibrin formation represents the most powerful surfactant-inhibitory mechanism hitherto described. Generation of a fibrin clot in the presence of pulmonary surfactant resulted in an almost complete incorporation of hydrophobic surfactant components, such as phospholipids and the surfactant proteins SP-B and SP-C, into the nascent fibrin matrix together with severe loss of surface tension-lowering properties. In addition, surfactant-containing fibrin represents a unique structure within the alveolar space with distinct properties. Compared to "normal" (extra-alveolar) fibrin clots, alveolar fibrin clots are characterized by altered clot architecture, altered mechanical properties and a reduced susceptibility towards proteolytic degradation (reviewed in [1]).

Thus, a correction of the hemostatic imbalance described above by increasing the alveolar fibrinolytic activity may represent a reasonable therapeutic approach to restore surfactant function. And indeed, in vivo and in vitro studies have succeeded in achieving this goal. An up-regulation of urokinase levels by adenovirus-mediated gene transfer reduced the extent of bleomycin-induced lung fibrosis in mice [16]. Furthermore, in perfused rabbit lungs urokinase treatment was followed by a pronounced improvement of gas exchange [17]. In vitro cleavage of surfactant-incorporating fibrin was shown to rescue surfactant material trapped in the fibrin matrix, with its surface tension-lowering properties being conserved [18, 19].

This strategy, however, might be hampered by induction of bleeding from pulmonary and extra-pulmonary sites, even if the fibrinolytic agent is primarily distributed to the alveolar space. Moreover, disadvantageous effects on surfactant function might be provoked. To overcome these limitations tools have to be developed which enhance the selectivity and potency of a fibrinolytic therapy against surfactant-containing fibrin.

Ruppert et al. have recently established such a molecular tool for targeting alveolar fibrin by chemically coupling a monoclonal anti-SP-B antibody, designated 8B5E, to human urokinase using a heterobifunctional cross-linker [20]. In another study [21], the same authors have reported chemical cross-linking of human urokinase to purified bovine SP-B. Both of these hybrid proteins were found: (1) to retain the biophysical activities compared to native SP-B, and (2) to be about 2-3 fold more effective in lysis of surfactant-containing fibrin clots and about 3-5 fold more resistant towards PAI-1 than native u-PA, thus resulting in chimeric enzymes with enhanced substrate specificity. On the other hand, due to the effort required to purify the proteins, in particular with respect to SP-B, which is purified from a natural source, to be coupled by conventional purification methods, this strategy is time-consuming and quite laborious. This disadvantage, however, may be partially overcome by the recombinant production of the two isolated proteins (e.g. urokinase and SP-B), followed by their chemical cross-linking.

For this purpose, recombinant mature SP-B might be obtained by according to U.S. Patent [22]. This patent discloses a process for producing mature alveolar SP-B using a SP-B precursor protein having a propeptide only at its N-terminus but lacking a C-terminal propeptide. In [22], processing of the N-terminal propeptide is performed in vitro using a genetically engineered hydroxylamine cleavage site. This results in release of the mature peptide.

Recombinant human urokinase might be obtained in accordance with U.S. Patent [23]. Furthermore, hybrid plasminogen activators have been disclosed, e.g., in the following U.S. patents: [24] describes a fibrinolyticaily active two-chain hybrid protein, wherein the chains are derived from the same or different two-chain proteases. U.S. Patent [25] describes a fibrin-specific two-chain urokinase-plasminogen activator in a therapeutic dosage form for dissolving clots in vivo, whereas [26] discloses the recombinant production of single-chain chimeric plasminogen activators composed of at least two subsequences of human tissue-plasminogen activator and human urokinase-plasminogen activator. The plasminogen activators disclosed in [23-26] are only for systemic application.

Another desirable feature of an efficient fibrinolytic tool for targeting alveolar fibrin would be its specificity for surfactant-containing fibrin clots. U.S. Patent [27] describes a fusion protein of lysozyme and the C-terminal propeptide of SP-B with the ten preceding amino acid residues of the mature SP-B peptide included, which is administered in a pharmaceutically acceptable medium to an individual to prevent and/or treat bacterial infections, particularly bacterial respiratory infections. By fusing lysozyme to a portion of a surfactant protein, the enzyme is delivered to the lung as the target infection site. Thus, according to [27] a SP-B fragment can be employed to target an enzymatic activity that is fused to it to a confined region of the body.

Accordingly, there is still a need for molecular tools suitable for a fibrinolytic therapy against surfactant-containing fibrin. Although the two hybrid proteins described above [20, 21] are actually functional, they have some pivotal drawbacks: First, chemical coupling requires purification of the proteins to be coupled which can be very laborious and time-consuming for its own (see above). Second in the vast majority of cases the precise composition and/or structure of the conjugate obtained is unknown due to ambiguities regarding the amino acid residues actually undergoing coupling events. Third, not every protein and every cross-linking agent are applicable to chemical coupling in a given experimental setting, and fourth the efficiencies of the coupling step may vary among experiments of the same type.

Therefore, the problem to be solved by the present inventions is to overcome these limitations and to provide a molecular tool, which not only specifically targets surfactant-containing fibrin clots and efficiently lyses such clots but which can also be produced easily in amounts sufficient for therapeutic applications.

These goals are accomplished by a fusion protein having the features of the independent claims as well as by the method for their production. Such a fusion protein comprises:
(a) a mammalian surfactant protein precursor lacking its C-terminal propeptide, and
(b) a mammalian plasminogen activator,
wherein the surfactant protein precursor is fused at its C-terminus to the N-terminus of the plasminogen activator.

Alternatively, a fusion protein of the present invention comprises:
(a) a mature mammalian surfactant protein, and
(b) a mammalian plasminogen activator,
wherein the mature surfactant protein is fused at its C-terminus or its N-terminus to the N-terminus or the C-terminus of the plasminogen activator, respectively.

Such "single-chain" fusion proteins of the present invention (compared to the "two-chain" hybrid proteins generated by chemical coupling) appear to retain both the biophysical properties of the surfactant protein and the fibrinolytic activity of the plasminogen activator, and they are efficiently targeted to intra-alveolar surfactant-containing fibrin clots. Furthermore, the present invention provides the advantage that the subsequent purification of the nascent recombinant protein is also straightforward and can normally be performed within a day. Additionally, by employing this recombinant method it is assured that the fusion proteins are assembled in a 1:1 fashion, i.e. have a defined composition.

Considering the synthesis and processing of the surfactant proteins SP-B and SP-C in vivo, the apparent retention of the biophysical properties of the surfactant protein by the inventive fusion protein is particularly surprising since it contains the N-terminal propeptide of the mammalian surfactant protein. Both SP-B and SP-C are synthesized as precursor proteins by type II alveolar cells. These precursors are processed to the mature peptides during transit through the secretory pathway (reviewed in [9, 10, 12]). Due to the hydrophobicity of mature SP-B and SP-C, respectively, it is physiologically indispensable to escort them in form of precursor proteins prior to association with surfactant lipids. Otherwise, they would immediately disrupt lipid membranes, which would in turn result in cell lysis (for this reason, it has so far not been possible to produce recombinant mature SP-B in cell cultures systems such as HeLa or CHO cells).

Therefore, it must be assumed that the propeptide prevents the mature surfactant protein from exhibiting its biophysical activity during the delivery to the alveolar cells, meaning that the propeptide provides in some respect on the molecular level a "shield" against the (at that time highly detrimental) function and cell damaging properties of the mature surfactant protein. Accordingly, it was to the surprise of the inventors to find out that despite the presence of the N-terminal propeptide the fusion proteins of the invention appear to possess the biophysical properties of the mature surfactant protein.

The fusion proteins of the invention are generated by means of recombinant DNA technology, which allows complete control of the sequence of an individual fusion protein and thus of its biophysical characteristics. Mutations within the amino acid sequence can be accomplished very easily on DNA level using established standard methods [28].

Possible alterations of the amino acid sequence are insertions or deletions as well as amino acid substitutions. Such substitutions may be conservative, i.e. an amino acid residue is replaced with a chemically similar amino acid residue. Compilations of the properties of amino acid residues are well known in the art. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

One the other hand, it is also possible to introduce non-conservative alterations in the amino acid sequence. Since SP-B, for example, is rich in cysteine residues, which form inter- as well as intramolecular disulfide bridges, one such substitution could be the replacement of a cysteine residue with alanine to prevent the formation of disulfide bridges that may interfere with the biophysical and/or catalytic properties of the inventive fusion proteins. Another possible substitution could be the replacement of one or more valine residues of SP-C, e.g., with glycine in order to reduce the hydrophobicity of this protein. However, it is not only possible to change single amino acid residues but also complete domains of the fusion protein according to the invention. For example, portions of the protein that are not involved in catalysis and are not crucial for folding into a functional three-dimensional structure could be removed to reduce the size of the fusion protein, which may be advantageous in many respects.

In general, such modifications of the amino acid sequence are intended to improve the biophysical characteristics and/or the catalytic properties of the inventive fusion protein (e.g., the half-life in vivo, the membrane permeability or its acid resistance in the case of oral administration).

The terms "precursor protein" or "precursor" as used herein refer to a protein that is not completely processed to its mature form but still comprises its N- and/or C-terminal propeptides. The terms "protein component" or "component" refer to the surfactant protein precursors as well as plasminogen activators comprising the fusion proteins of the invention.

In preferred embodiments of the invention, at least one component of the fusion protein as disclosed herein, i.e. the surfactant protein component and the plasminogen activator component, respectively, is a human protein. Most preferred are fusion proteins wherein both components are human proteins (see also FIG. 2).

The invention also includes fusion proteins comprising components, which differ from what is referred to as "wild-type" protein as a result of alternative splicing of a common pre-mRNA molecule, but are nevertheless functional.

The surfactant protein component of the fusion protein may be any known surfactant protein, i.e. surfactant protein SP-A, -B, -C, or -D, with the hydrophobic proteins SP-B and SP-C being preferred, and with SP-B being most preferred. As already outlined above, fibrin formation in the presence of pulmonary surfactant has been shown to result in an almost complete incorporation of these two proteins into the fibrin clot, which makes them suitable candidates for targeting another protein, in this case a plasminogen activator, to surfactant containing clots.

The SP-B precursor (the polypeptide encoded by the nucleic acid sequence shown as SEQ ID NO: 1) comprises the "mature peptide" (79 amino acids) flanked by a 200 amino acid N-terminal propeptide (including a 23 amino acid signal peptide) and a 102 amino acid C-terminal propeptide, respectively. The fragment comprising the N-terminal propeptide and the mature peptide (the polypeptide encoded by the nucleic acid sequence shown as SEQ ID NO: 2) was demonstrated to be necessary and sufficient for both correct folding and transport of SP-B. The removal of the N-terminal propeptide and release of mature SP-B (the polypeptide encoded by the nucleic acid sequence shown as SEQ ID NO: 3) occurs in type II alveolar cells. So far, it has not been possible to produce mature SP-B in any conventional cell culture systems, such as HeLa cells or CHO cells (cf. above).

Thus, in a preferred embodiment of the invention, the surfactant protein component of the fusion protein is the polypeptide encoded by the nucleic acid sequence shown as SEQ ID NO: 2.

In an alternative preferred embodiment of the invention, the surfactant protein component of the fusion protein is the polypeptide encoded by the nucleic acid sequence shown as SEQ ID NO: 3.

The post-translational processing of the SP-C precursor (the polypeptide encoded by the nucleic acid sequence shown as SEQ ID NO: 8) is very similar to that of SP-B. Mature SP-C (the polypeptide encoded by the nucleic acid sequence shown as SEQ ID NO: 10), a small protein of only 35 amino acids, is produced by subsequent cleavage of the C- and N-terminal propeptide, respectively (reviewed in [9,10,12]).

In another preferred embodiment of the invention, the surfactant protein precursor of the fusion protein is SP-C (the polypeptide encoded by the nucleic acid sequence shown as SEQ ID NO: 9).

In a further preferred embodiment of the invention, the surfactant protein component of the fusion protein is the polypeptide encoded by the nucleic acid sequence shown as SEQ ID NO: 10.

A preferred fusion partner for SP-B and SP-C, respectively, with regard to an object of the invention, i.e. lysis of surfactant containing fibrin clots, is urokinase-plasminogen activator (u-PA), since it is the predominant plasminogen activator in the alveolar space. Urokinase-plasminogen activator is synthesized as a 411 amino acid precursor protein as well, which is termed single-chain u-PA (or pro-urokinase; the polypeptide encoded by the nucleic acid sequence shown as SEQ ID NO: 4). Cleavage between Lys-158 and Ile-159 results in the formation of high molecular weight two-chain u-PA (HMW-u-PA). Further processing by cleavage between Lys-135 and Lys-136 generates low molecular weight two-chain u-PA (LMW-u-PA; the polypeptide encoded by the nucleic acid sequence shown as SEQ ID NO: 5), which is reported to have a similar enzymatic activity as the high molecular weight form. The two chains of the protein are connected by a disulfide-bridge between Cys-148 and Cys-279. However, it is possible to use in the present invention any proteinaceous plasminogen activator or fragment or mutant thereof as long as this polypeptidic molecule has plasminogen activator activity.

In a further preferred embodiment of the invention, the plasminogen activator of the fusion protein is the LMW-u-PA polypeptide the polypeptide encoded by the nucleic acid sequence shown as SEQ ID NO: 5.

Figure 1B:
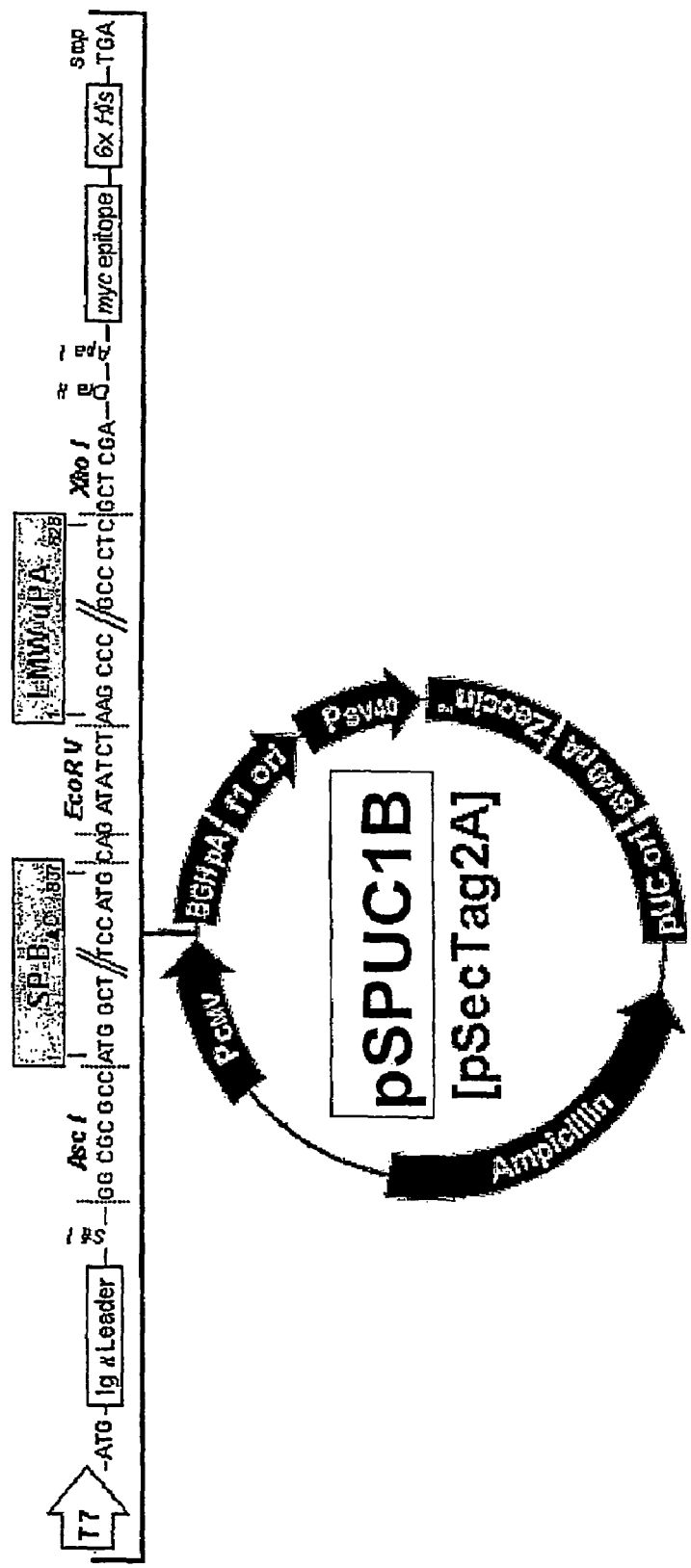

Most preferably, the fusion protein of the invention is a polypeptide encoded by a nucleic acid sequence selected from the group consisting of SEQ ID NO: 6 and SEQ ID NO: 7 comprising chimeras of the SP-B precursor (SP-B$_{Ac}$) and LMW-u-PA, which are referred to as SPUC1A and SPUC1B, respectively (see also FIGS. 1A and 1B).

Figure 1C:
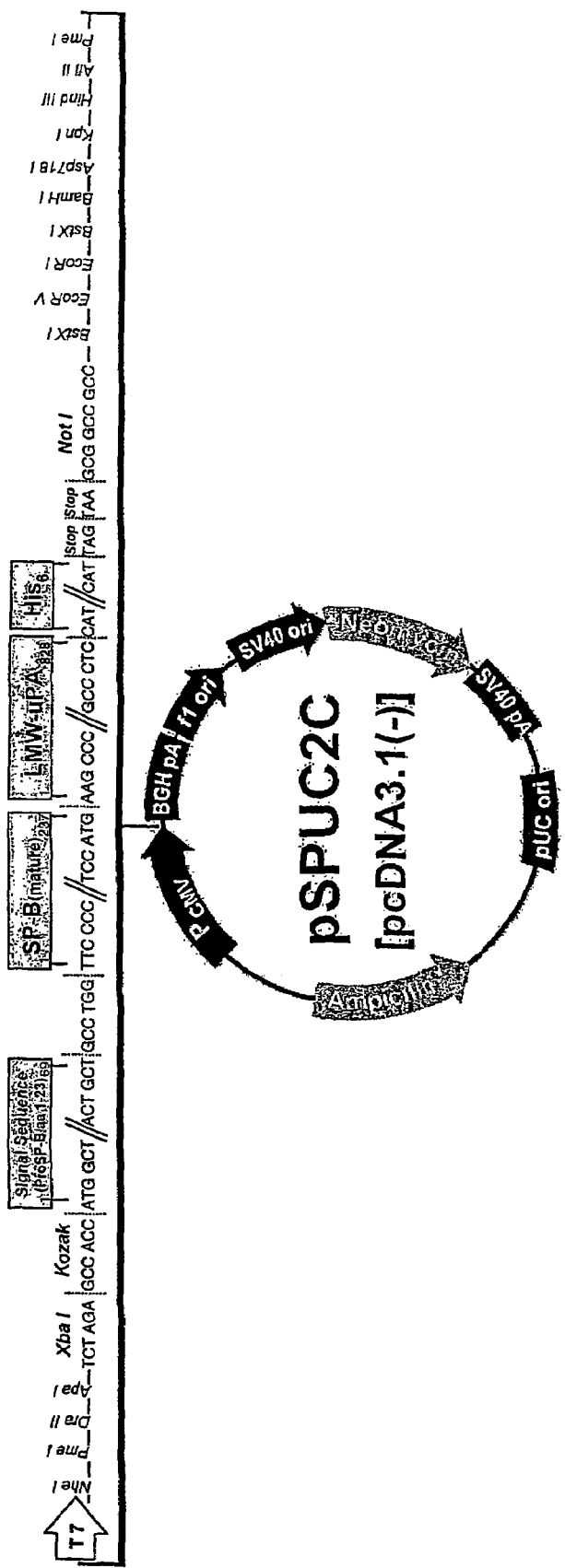
Figure 1D:
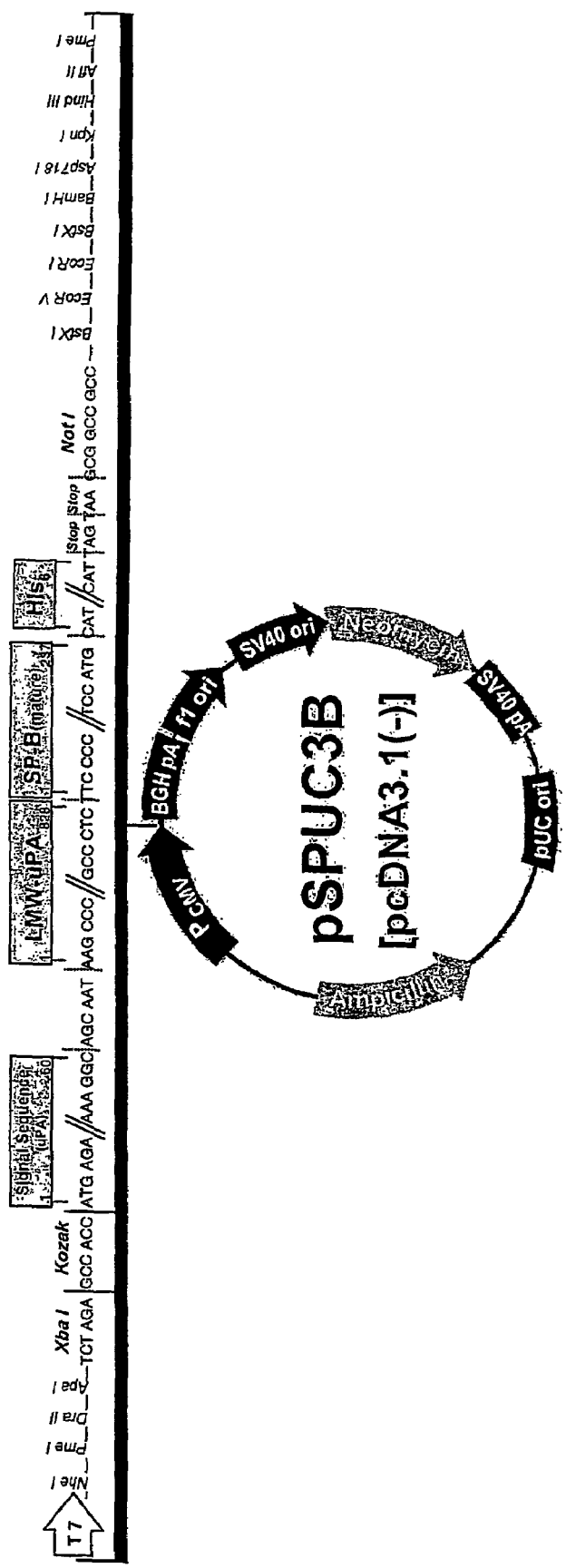

In another particular preferred embodiment of the invention, the fusion protein is a polypeptide encoded by a nucleic acid sequence selected from the group consisting of SEQ ID NO: 12 and SEQ ID NO: 13 comprising chimeras of the mature SP-B (SP-Bmature) and LMW-u-PA, which are referred to as SPUC@C and SPUC3B, respectively (see also FIGS. 1C and 1D).

Also preferred is a fusion protein comprising tissue-plasminogen activator (t-PA; the polypeptide encoded by the nucleic acid sequence shown as SEQ ID NO: 11) as the plasminogen activator component.

Figure 2:
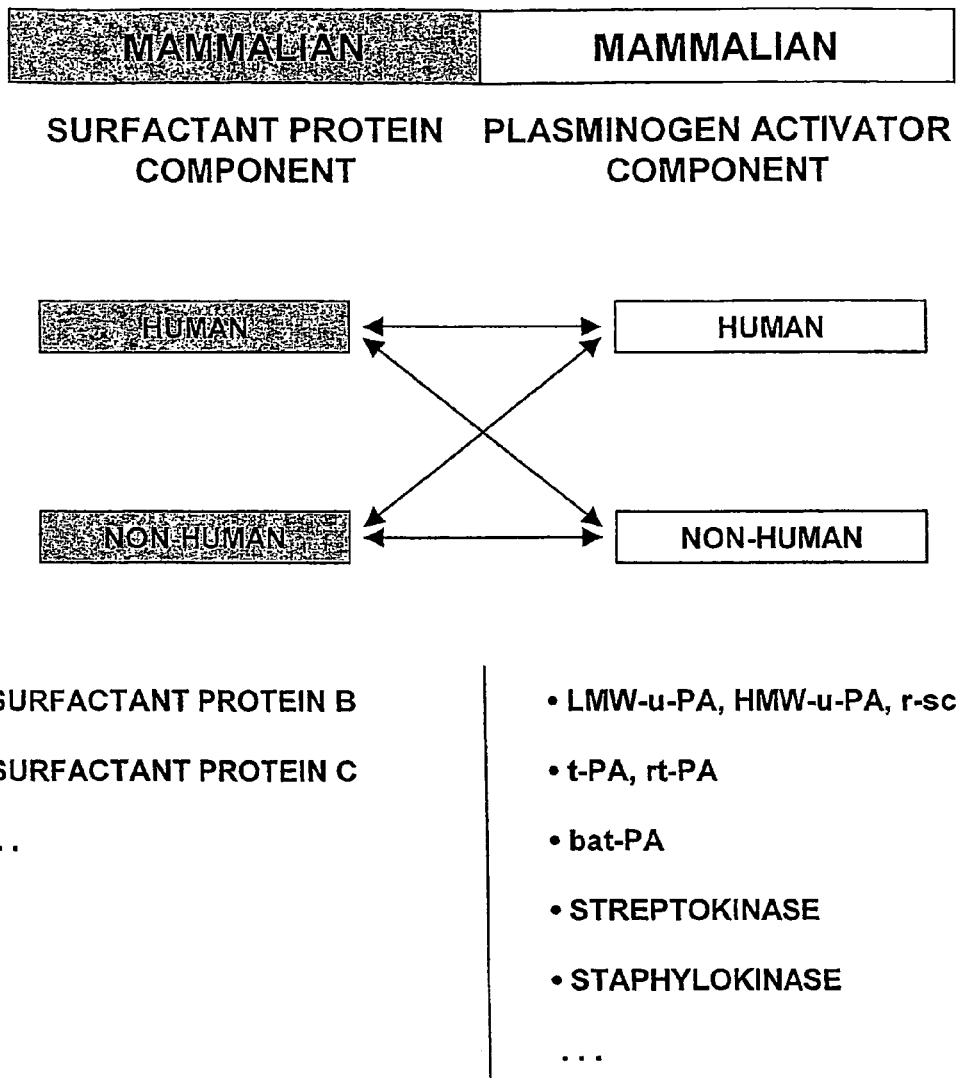

Additional non-limiting examples of plasminogen activators suitable for fusion proteins according to the invention are: high molecular weight two-chain u-PA (HMW-u-PA), LMW-u-PA B-chain, recombinant single-chain u-PA (r-scu-PA), recombinant t-PA (rt-PA), and its variants r-PA, n-PA, and TNK-t-PA, desmodus salivary plasminogen activator α-1 (bat-PA), streptokinase, staphylokinase, and catalytically active mutants thereof. Examples of suitable plasminogen activators are also illustrated in FIG. 2.

In a further preferred embodiment of the invention the fusion protein carries a protein or peptide affinity tag at its N-terminus and/or at its C-terminus in order to allow easy detection and/or purification of the recombinant protein. Suitable affinity tags are, for example, the myc-tag, the FLAG-tag, the $His_6$-tag (SEQ ID NO: 27), the Strep-Tag® or the HA-tag.

The present invention also relates to nucleic acid molecules (DNA and RNA) comprising nucleotide sequences coding for fusion proteins as described herein. Since the degeneracy of the genetic code permits substitutions of certain codons by other codons specifying the same amino acid, the invention is not limited to a specific nucleic acid molecule encoding a fusion protein of the invention but includes all nucleic acid molecules comprising nucleotide sequences encoding a functional fusion protein.

The invention also includes nucleic acid molecules encoding a functional fusion protein that comprises nucleic acid sequences different from what is referred to as "wild-type" nucleic acid sequence due to alternative splicing of a common pre-mRNA molecule. Such splicing events include the alternative use of exons (i.e. nucleic acid sequences encoding an amino acid sequence), exon shuffling (i.e. an alternative arrangement of exons), and the retention of introns (i.e. intervening sequences normally not encoding an amino acid sequence) within the mature mRNA molecule.

In preferred embodiments of the invention at least one component of the fusion protein, i.e. the surfactant protein component and the plasminogen activator component, respectively, is encoded by a human nucleic acid sequence. Most preferred are fusion proteins wherein both components are encoded by human nucleic acid sequences (see also FIG. 2).

In another preferred embodiment the nucleic acid sequence encoding the surfactant protein component of the fusion protein as disclosed herein is selected from the group consisting of SEQ ID NO: 2 and SEQ ID NO: 9, with the former one preferred.

Also preferred are the nucleic acid sequences encoding a fusion protein as disclosed herein, wherein the surfactant protein component is selected from the group consisting of SEQ ID NO: 3 and SEQ ID NO: 10, with the former one preferred.

Most preferably, the nucleic acid molecule comprises a nucleic acid sequence selected from the group consisting of SEQ ID NO: 6 and SEQ ID NO: 7 (see also FIGS. 1A and 1B).

In a further particular preferred embodiment of the invention, the nucleic acid molecule comprises a nucleic acid sequence selected from the group consisting of SEQ ID NO: 12 and SEQ ID NO: 13 (see also FIGS. 1C and 1D).

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, preferably a promoter sequence. In another preferred embodiment, a nucleic acid molecule of the invention comprises a promoter sequence and a transcriptional termination sequence. Suitable prokaryotic promoters are, for example, the lacUV5 promoter or the T7 promoter. Examples of promoters useful for expression in eukaryotic cells are the SV40 promoter or the CMV promoter.

The nucleic acid molecules of the invention can also be comprised in a vector or other cloning vehicles, such as plasmids, phagemids, phage, baculovirus, cosmids or artificial chromosomes. In a preferred embodiment, the nucleic acid molecule is comprised in a vector, particularly in an expression vector. Such an expression vector can include, aside from the regulatory sequences described above and a nucleic acid sequence encoding a fusion protein of the invention, replication and control sequences derived from a species compatible with the host that is used for expression as well as selection markers conferring a selectable phenotype on transformed or transfected cells. Most preferably, the nucleic acid molecule is comprised in an expression vector adapted for expression of a eukaryotic coding sequence. Large numbers of suitable vectors are known in the art, and are commercially available.

The DNA molecule encoding fusion proteins of the invention, and in particular a vector containing the coding sequence of such a fusion protein can be transformed into a host cell capable of expressing the gene. Transformation can be performed using standard techniques [28]. Thus, the invention is also directed to a host cell containing a nucleic acid molecule as disclosed herein.

The transformed host cells are cultured under conditions suitable for expression of the nucleotide sequence encoding a fusion protein of the invention. Suitable host cells can be prokaryotic, such as *Escherichia coli* (*E. coli*) or *Bacillus subtilis*, or eukaryotic, such as *Saccharomyces cerevisiae, Pichia pastoris*, SF9 or High5 insect cells, immortalized mammalian cell lines (e.g. HeLa cells or CHO cells), primary mammalian cells or pulmonary stem cells.

The invention also relates to a method for recombinant production of fusion proteins according to the invention. This method comprises:
  (a) introducing a nucleic acid molecule encoding the fusion protein into a suitable vector, and
  (b) introducing the recombinant vector obtained in (a) into a suitable host cell or into a suitable cell extract.

Step (a) can be performed with a nucleic acid molecule encoding only the fusion protein. Alternatively, it can be performed with a nucleic acid molecule in which the fusion protein coding sequence is operably linked to regulatory sequences. Optionally, the nucleic acid molecule of the invention can also be fused to a sequence coding for a fusion partner such as an affinity tag allowing easy detection and/or purification of the recombinant fusion protein. In another embodiment of the method of the invention, the nucleic acid sequences encoding the surfactant protein and the plasminogen activator component, respectively, of the fusion protein as disclosed herein may be independently from each other inserted into a suitable vector. Gene expression can be achieved in a recombinant cell or a suitable cell extract, which contains all factors required for transcription and translation.

Furthermore, the present invention refers to pharmaceutical uses of the inventive fusion protein. In one embodiment, the invention refers to a method for prophylaxis and/or treatment of inflammatory and interstitial lung diseases, comprising the step of administering a fusion protein as disclosed herein alone or in combination with other pharmaceutically active compounds and a pharmaceutically acceptable excipient to a mammal, and in particular to a human.

Acute or chronic inflammatory and interstitial lung diseases or lung disorders which may be prevented or treated with a fusion protein described in this application include the acute (or adult) respiratory distress syndrome (ARDS), acute lung injury (ALI), interstitial lung disease (ILD), idiopathic pulmonary fibrosis (IPF), sarcoidosis, hypersensitivity pneumonitis, pulmonary inflammation, pneumonia, bronchitis, asthma, cystic fibrosis, surfactant abnormalities in recurrent apparent life-threatening events (ALTE) or the sudden infant death syndrome (SIDS), congenital alveolar proteinosis and the severe acute respiratory syndrome (SARS).

The fusion proteins according to the invention can be administered via any parenteral, non-parenteral (enteral) or topical (intratracheal) route that is therapeutically effective for proteinaceous drugs. Parenteral application methods comprise, for example, intracutaneous, subcutaneous, intramuscular or intravenous injection and infusion techniques, e.g. in the form of injection solutions, infusion solutions or tinctures, as well as aerosol installation and inhalation, e.g. in the form of aerosol mixtures, sprays or dry powders. Non-parenteral delivery modes are, for instance, orally; e.g. in the form of pills, tablets, capsules, solutions or suspensions, or rectally, e.g. in the form of suppositories. The fusion proteins of the invention can be administered systemically or topically in formulations containing conventional non-toxic pharmaceutically acceptable excipients or carriers, additives and vehicles as desired.

In a preferred embodiment of the present invention the fusion protein is administered parenterally to a mammal, and in particular to humans, with aerosol administration or intratracheal installation being the most preferable application method.

The dosage of the fusion protein of the present invention may vary within wide limits to achieve the desired therapeutic response for a particular patient. It will, for instance, depend on the enzymatic, i.e. fibrinolytic, activity of the fusion protein as well as its half-life in vivo, the mode of administration, the severity of the disease/disorder being treated, as well as the medical condition of the patient. For example, treatment of acute short-term disorders, such as an asthmatic attack or acute lung injury, might be best accomplished when using a dose as high as maintainable. In contrast, for treatment of long-term chronic disorders, such as interstitial lung disease or idiopathic pulmonary fibrosis, a lower dosage, optionally given in a sustained release formulation, might be more suitable. The establishment of a therapeutically effective dosage amount for a given individual is within the level of skill in the art.

In general, a daily dose of about 500 μg to 200 mg fusion protein per kilogram body weight may be appropriate. Preferred dosage levels range from 0.5 mg to 50 mg/kg body weight/day for a long-term regimen and from 50 mg to 200 mg/kg body weight/day for short-term treatments. The fusion protein can be applied as a single dose or may be divided into several, e.g., two to four, part administrations.

Thus, the invention is also directed to a pharmaceutical composition comprising a fusion protein as described above and a pharmaceutically acceptable excipient. In particular, the invention refers to a pharmaceutical composition, which has fibrinolytic activity.

Recombinant fusion proteins of the invention can be formulated into compositions using pharmaceutically acceptable ingredients as well as established methods of preparation [29]. To prepare the pharmaceutical compositions, pharmaceutically inert inorganic or organic excipients can be used. To prepare e.g. pills, powders, gelatin capsules or suppositories, for example, lactose, talc, stearic acid and its salts, fats, waxes, solid or liquid polyols, natural and hardened oils. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes, nanoparticles, and microcapsules.

For example, fusion proteins of the invention can be admixed to commercially available surfactant preparations and administered by aerosol administration or transbronchial instillation or via a bronchoscope. Suitable surfactant preparations include, e.g., Survanta® as well as Alveofact®, two natural bovine surfactant preparations, Infasurf®, a calf-lung surfactant extract, and Exosurt®, a synthetic surfactant composition lacking the hydrophobic proteins SP-B and SP-C.

The invention is further illustrated by the following non-limiting Figures and Examples.

FIG. 1 shows schematic representations of four exemplary expression vectors according to the invention. The vectors illustrated in FIGS. 1A and 1B encode fusion proteins consisting of SP-$B_{\Delta c}$ N-terminally fused to LMW-u-PA (SEQ ID NO: 6 and SEQ ID NO: 7, respectively). pSPUC1A (FIG. 1A) is derived of pcDNA3.1(−) (Invitrogen), whereas pSPUC1B (FIG. 1B) is derived of pSecTag2A (Invitrogen). FIG. 1C illustrates pSPUC2C encoding a fusion protein composed of SP-$B_{mature}$ N-terminally fused to LMW-u-PA (SEQ ID NO: 12), wherein this gene fusion is preceeded by a segment encoding the SP-B signal peptide as well as a 6-nucleotide spacer element. FIG. 1D depicts vector pSPUC3B encoding a fusion protein consisting of SP-$B_{mature}$ C-terminally fused to LMW-u-PA (SEQ ID NO: 13), wherein the LMW-u-PA cDNA is preceeded by a segment encoding the u-PA signal peptide as well as a 6-nucleotide spacer element. FIG. 1A discloses SEQ ID NOS 28-30, respectively, in order of appearance. FIG. 1B discloses SEQ ID NOS 31-33 and 27, respectively, in order of appearance. FIG. 1C discloses SEQ ID NOS 27 and 34-37, respectively, in order of appearance. FIG. 1D discloses SEQ ID NOS 27, 38-40 and 37, respectively, in order of appearance.

FIG. 2 schematically illustrates the design of a fusion protein according to the invention. A mammalian surfactant protein component is fused at its C-terminus to the N-terminus of a mammalian plasminogen activator. Either one of these components or both can be human proteins. The two protein components can be selected from the non-limiting examples indicated at the bottom part of the Figure. Importantly, if the surfactant protein component is a mature surfactant protein, it is also within the scope of the invention that the mature surfactant protein can be fused with its N-terminus to the C-terminus of a plasminogen activator.

Figure 3:
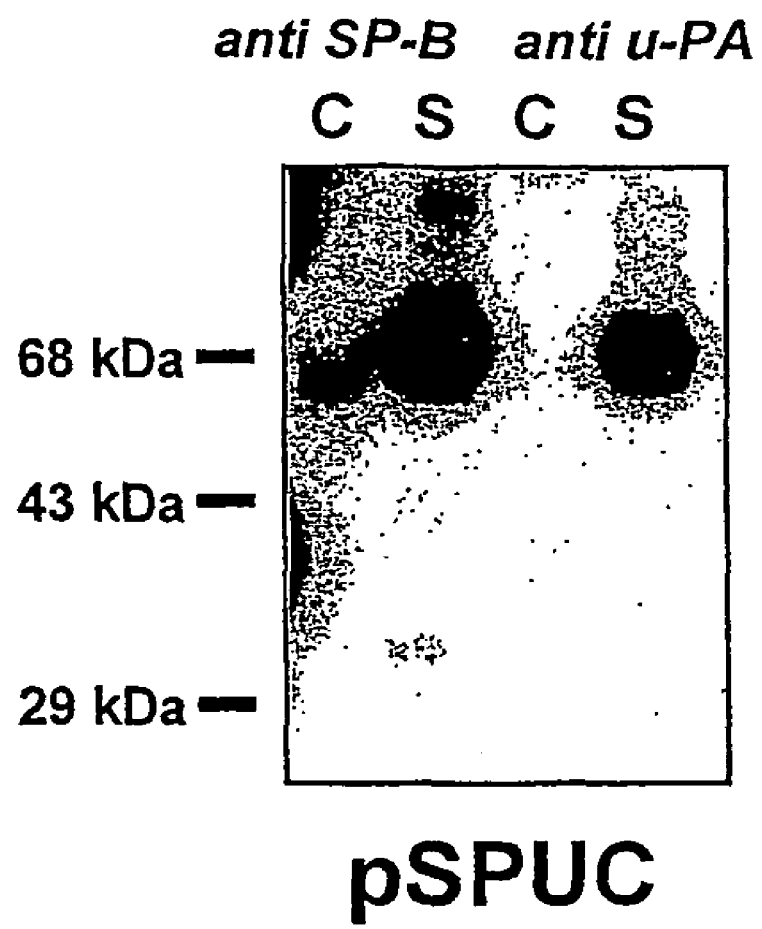

FIG. 3 documents successful expression of recombinant SPUC1A (SEQ ID NO: 6) in Chinese hamster ovary (CHO) cells. 35 hours following transfection with pSPUC, cells were harvested and labeled with [$^{35}$S]-methionine/cysteine for 6 hours. Supernatants (S) and cell lysates (C) were immunoprecipitated with the antibodies indicated, and bound proteins were separated by SDS-PAGE. Signals were visualized by autoradiography. A fusion protein of correct size (about 65 kDa) could be concordantly detected with antibodies specific for both components of the protein, respectively.

Figure 4:
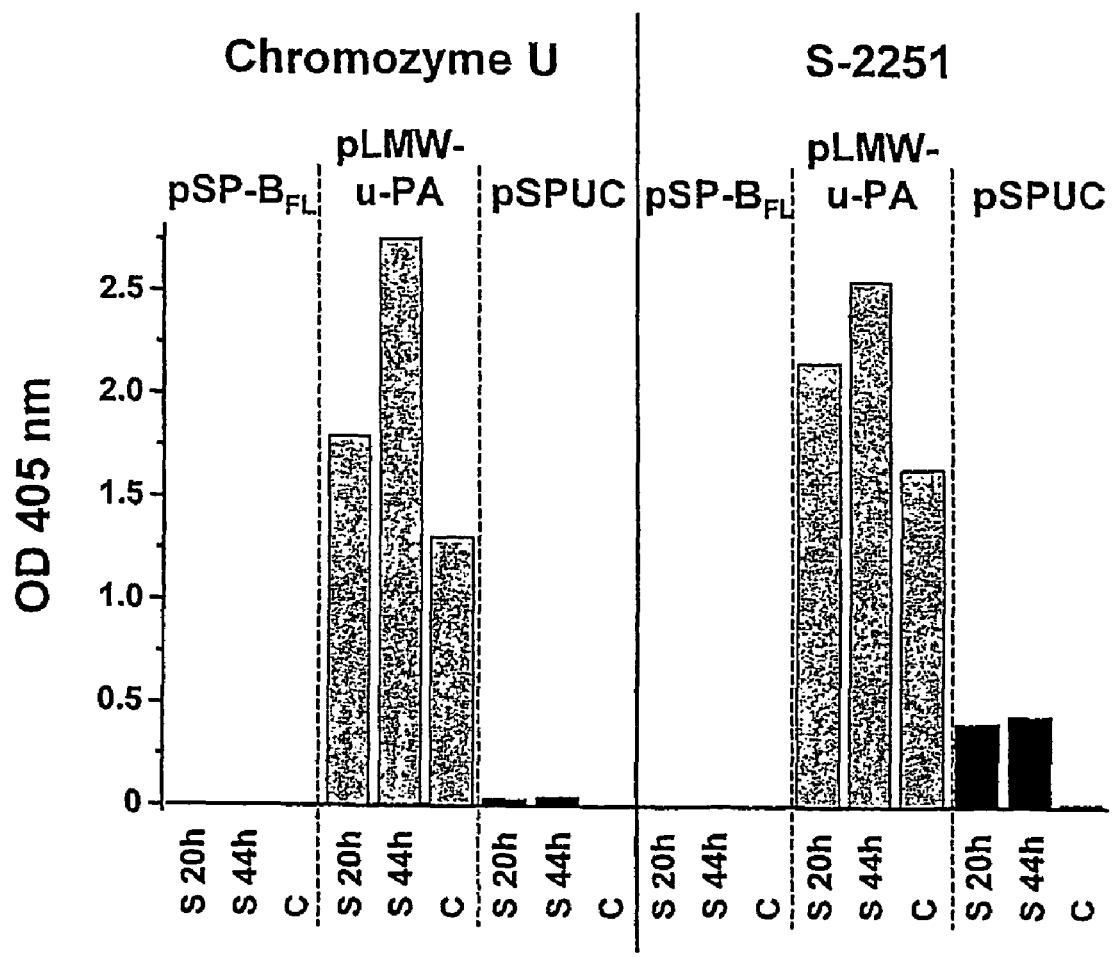

FIG. 4 depicts the amidolytic activity of SPUC1A (SEQ ID NO: 6) compared to full-length SP-B (SP-B$_{FL}$; SEQ ID NO: 1) and LMW-u-PA (SEQ ID NO: 5) in CHO cells. Cell samples were harvested either 20 hours (supernatants, S) or 44 hours (supernatants, S and cell lysates, C) after transfection with the respective DNAs, transferred to microtiter plates and incubated with the chromogenic substrates, Chromozyme U (direct substrate for u-PA) and S-2251 (indirect substrate, addition of plasminogen required), respectively. The absorbance (405 nm) of the samples was determined in a microplate reader. Cells transfected with pSPUC1A exhibited amidolytic activity, which was more pronounced after the addition of plasminogen. Thus, recombinant SPUC is functional when expressed in CHO cells.

EXAMPLE 1

Cloning of SPUC1A cDNA

The vector pSPUC1A (FIG. 1A) encoding a fusion protein (termed SPUC1A; SEQ ID NO: 6) consisting of human SP-B$_{AC}$ (SEQ D NO: 2) N-terminally fused to human low molecular weight urokinase-plasminogen activator (LMW-u-PA; SEQ ID NO: 5) was constructed using standard methods [28]. The respective cDNA fragments were inserted into the multiple cloning site of the expression vector pcDNA3.1(−) (Invitrogen) under control of the CMV promoter. The SP-B$_{AC}$ cDNA was cloned between the XhoI and HindIII sites of the multiple cloning site, and the LMW-u-PA cDNA between the HindIII and AflII sites.

The ligation mixture obtained was transformed into *E. Coli*, and single clones were screened for presence of the correct insert by PCR analysis using primers flanking the site of insertion. Positive transformants were amplified in *E. coli*. The vector-DNA was purified by ion-exchange chromatography and sequenced using an automated system (ABI Prism 310 Genetic Analyzer; Perkin Elmer).

EXAMPLE 2

Expression of SPUC1A in CHO Cells

Chinese hamster ovary (CHO) cells (American Type Culture Collection) were grown as monolayers at 37° C. and 10% CO$_2$. Growth medium consisted of a 1:1 mixture of DM and DMEM-F12 supplemented with 10% fetal calf serum, 20 mM glutamine, 100 U/ml penicillin, and 100 µg/ml streptomycin. DNA transfection was performed using 2.5 µg pSPUC1A and Lipofectamine Plus (Life Technologies/GIBCO BRL) according to the instructions of the manufacturer.

The expression of SPUC1A (SEQ ID NO: 6) was analyzed using [$^{35}$S] cell labeling and immunoprecipitation (FIG. 3). 35 h following transfection, the growth medium was replaced with DMEM supplemented with 10% FCS and 25 mM HEPES, but free of methionine/cysteine. After a 40 min incubation period, the cells were labeled for 6 h with 0.5 mCi/ml [$^{35}$S]-methionine/cysteine (Pro-mix [$^{35}$S] in vitro cell labeling mix; Amersham).

Supernatants (S) as well as cell lysates (C) were then immunoprecipitated with a polyclonal rabbit anti-human pro-SP-B antibody (Chemicon) and a monoclonal mouse anti-human u-PA antibody (American Diagnostica), respectively. Protein G-Sepharose (30 µl; Zymed Laboratories) and rabbit serum (5 µl) were added to each tube and the samples incubated on a rotator at 4° C. for 12 h. After centrifugation at 1.000×g, the supernatants were transferred to new tubes, and 30 µl Protein-G-Sepharose and 5 µl of the respective antibody were added. After another incubation period (12 h, 4° C.) and subsequent centrifugation, the pellets were washed four times with wash buffer A (150 mM NaCl, 50 mM Tris, 5 mM EDTA, 0.1% Triton X-100, 0.02% SDS, pH 7.6) and twice with wash buffer B (150 mM NaCl, 50 mM Tris, 5 mM EDTA, pH 7.6). The samples were suspended in Laemmli-buffer, boiled for 5 ml, and run on a 10% SDS-PAGE gel. The gel was fixed for 1 h in 40% methanol/10% glacial acid/4% glycerol, incubated for 30 min in enhancer solution, dried in a vacuum chamber, and exposed to an X-ray film (Kodak Biomax MR).

A fusion protein of the expected size (about 65 kDa) could be concordantly detected with antibodies specific for both components of the protein, respectively (FIG. 3). Thus, recombinant SPUC1A can be successfully expressed in CHO cells. A preliminary quantification of SPUC1A levels by ELISA analysis using the monoclonal mouse anti-human u-PA antibody (data not shown) resulted in concentrations ranging from 34 to 58 ng/ml supernatant.

EXAMPLE 3

Functional Analysis of SPUC1A Using Chromogenic Substrates

The amidolytic activity of recombinant SPUC1A (SEQ ID NO: 6) in CHO cell supernatants and lysates was determined using the chromogenic substrates Chromozyme U (Roche Diagnostics) and S-2251 (Chromogenix), respectively. The assay buffer consisted of 100 mM Tris, pH 7.6, 0.5% Tween-20, and 100 µg/ml BSA.

Chromozyme U is a direct substrate for u-PA. Test samples (cell supernatants 20 and 44 h after transfection as well as cell lysates) were transferred in a volume of 50 µl to a microtiter plate and incubated with 100 µl assay buffer and 100 µl Chromozyme U (1 mg/ml). Reactions were terminated by addition of 50 µl acetic acid (50% solution), and the absorbance was determined at 405 nm. S-2251, on the other hand, is an indirect substrate for u-PA that is cleaved after activation of plasminogen to plasmin. Test samples were also transferred to a microtiter plate and mixed with 100 µl of a diluted plasminogen solution (50 µg/ml) and 100 µl S-2251 (2 mM) dissolved in assay buffer. After incubation, reactions were terminated by addition of 50 µl acetic acid, and the absorbance at 405 nm was measured. Cells transfected with pSPB$_{FL}$ encoding human full-length SP-B (SEQ D NO: 1) served as negative control, whereas cells transfected with pLMW-u-PA encoding human LMW urokinase-plasminogen activator (SEQ ID NO: 5) served as positive control.

After transfection of CHO cells with pSPUC1A, amidolytic activity could be detected in the cell supernatants (FIG. 4). However, the effect was more pronounced after addition of plasminogen when using S-2251 as a substrate. In cells transfected with pSPB$_{FL}$ no measurable amidolytic activity was observed, as expected. Cells transfected with pLMW-u-PA showed much higher levels of u-PA activity compared to cells transfected with pSPUC1A. The reason for this finding remains unclear and has to be addressed in further studies. Nevertheless, these results confirmed that recombinant SPUC1A is indeed functional when heterogeneously expressed in CHO cells.

EXAMPLE 4

Functional Analysis of SPUC1A by Fibrin Gel Autography

As a second measure of plasminogen activator activity CHO cell supernatants and lysates were analyzed by fibrin gel autography, which was performed as described [30]. The samples were separated via SDS-PAGE using 10% acrylamide resolving gels. The gel was soaked for 1.5 h in 0.1 M sodium phosphate pH 7.2 with 5% Triton X-100 to neutralize SDS and then placed on top of a fibrin indicator gel. In brief, a 2% (w/v) agarose solution was boiled, cooled to 45° C. and mixed with pre-warmed phosphate-buffered saline containing 140 µg/ml plasminogen and 0.8 U/ml thrombin. Fibrinogen (10 mg/ml) in PBS (37° C.) was added and the mixture was poured onto a glass plate. Final concentrations were 1% agarose, 35 µg/ml plasminogen, 0.2 U/ml thrombin, and 2 mg/ml fibrinogen. The fibrin gel was developed in a moist chamber and photographed. Plasminogen activators were revealed by formation of dark lytic zones in the opaque fibrin matrix of the indicator gel.

In CHO cells transfected with pSPUC1A, a lytic zone migrating at about 65 kDa could be identified in both supernatants and cell lysates (data not shown). This finding is in full agreement with the results obtained in the cell labeling/immunoprecipitation studies (FIG. 3; Example 2) as well as the cleavage experiments (FIG. 4; Example 3) described above, further substantiating the functionality of recombinant SPUC1A.

The following references are cited in this document:
[1] Günther, A. et al. (2001) Respir. Res. 3, 353-364.
[2] Idell, S. (2002) Crit. Care Med. 30, S274-S280.
[3] Idell, S. et al. (1989) J. Clin. Invest. 84, 695-705.
[4] Bertozzi, P. et al. (1990) N. Engl. J. Med. 322, 890-897.
[5] Günther, A. et al. (2000) Am. J. Respir. Crit. Care Med. 161, 454-462.
[6] Campbell, E. J. et al. (1987) Chest 92, 161-167.
[7] Burkhardt, A. (1989) Am. Rev. Respir. Dis. 140, 513-524.
[8] Yamada, K. M. (1991) J. Biol. Chem. 266, 12809-12812.
[9] Creuwels, L. A. J. M. et al. (1997) Lung, 175, 1-39.
[10] Haagsman, H. P. and Diemel, R. V. (2001) Comp. Biochem. Physiol. A: Mol. Integr. Physiol. 129, 91-108.
[11] Crouch, E. and Wright, J. R. (2001) Annu. Rev. Physiol. 63, 521-554.
[12] Weaver, T. E. and Conkright, J. J. (2001) Annu. Rev. Physiol. 63, 555-578.
[13] International Publication WO 00/76535
[14] U.S. Pat. No. 5,006,343
[15] U.S. Pat. No. 5,302,581
[16] Sisson, T. H. et al. (1999) Hum. Gene Ther. 10, 2315-2323.
[17] Schermnuly, R. T. et al. (2001) Am. J. Physiol Lung Cell. Mol. Physiol. 280, L792-L800.
[18] Günther, A. et al. (1999) Am. J. Respir. Cell Mol. Biol. 21, 738-745.
[19] Markart, P. et al. (2003) Am. J. Physiol. Lung Cell. Mol. Physiol., 284, L69-L76.
[20] Ruppert, C. et al. (2002) Bioconjug. Chem. 13, 804-811.
[21] Ruppert, C. et al. (2003) Thromb. Haemost. 89, 53-64.
[22] U.S. Pat. No. 6,031,075
[23] U.S. Pat. No. 5,112,755
[24] U.S. Pat. No. 4,752,581
[25] U.S. Pat. No. 4,999,194
[26] U.S. Pat. No. 5,242,819
[27] U.S. Pat. No. 5,993,809
[28] Sambrook, J. et al. (1989) Molecular Cloning: A Laboratory Manual, 2nd Ed., Cold Spring Harbor Laboratory Press, Cold Spring Harbor, N.Y.
[29] Gennaro, A. L. and Gennaro, A. R. (2000) Remington: The Science and Practice of Pharmacy, 20th Ed., Lippincott Williams & Wilkins, Philadelphia, Pa.
[30] Levin, E. G. et al. (1983) J. Lab. Clin. Med. 102, 500-508.

The invention claimed is:

1. A fusion protein comprising:
   (a) a mammalian surfactant protein precursor lacking its C-terminal propeptide, and
   (b) a mammalian plasminogen activator,
   wherein the surfactant protein precursor is fused at its C-terminus to the N-terminus of the plasminogen activator, wherein the mammalian surfactant protein is surfactant protein B (SP-B), and wherein the fusion protein retains the biological activities of the surfactant protein and the plasminogen activator.

2. The fusion protein of claim 1 wherein one of the protein components (a) or (b) is a human protein.

3. The fusion protein of claim 1, wherein both protein components (a) and (b) are human proteins.

4. A fusion protein of claim 1, wherein the mammalian plasminogen activator is selected from the group consisting of high molecular weight two-chain urokinase-plasminogen activator (HMW-u-PA), low molecular weight two-chain u-PA (LMW-u-PA), low molecular weight u-PA B-chain, recombinant single-chain u-PA (r-scu-PA), tissue-plasminogen activator (t-PA), recombinant t-PA (rt-PA), its variants r-PA, n-PA, and TNK-t-PA, and catalytically active mutants of the plasminogen activator.

5. The fusion protein according to claim 1 comprising the surfactant protein B (SPB) precursor N-terminally fused to the low molecular weight two-chain u-PA (LMW-u-PA), as shown in SEQ ID NO: 19 and SEQ ID NO: 20, respectively.

6. The fusion protein of claim 1, further comprising one or more protein or peptide affinity tag tags at its positions selected from the N-terminus of the fusion protein, the C-terminus of the fusion protein, and both the N-terminus and C-terminus of the fusion protein.

7. A nucleic acid molecule comprising a nucleotide sequence encoding the fusion protein of claim 1.

8. The nucleic acid molecule according to claim 7, wherein the nucleic acid molecule is operably linked to a regulatory sequence to allow expression of the nucleic acid molecule.

9. The nucleic acid molecule according to claim 8, wherein the regulatory sequence comprises a promoter sequence and a transcription termination sequence.

10. A vector comprising the nucleic acid molecule of claim 7.

11. A host cell containing the nucleic acid molecule of claim 7.

12. A method for production of the fusion protein of claim 1, comprising:
   introducing a nucleic acid molecule encoding the fusion protein into a suitable vector, and
   introducing the recombinant vector into a suitable host cell or into a suitable cell extract under conditions suitable for the expression of said nucleic acid molecule encoding the fusion protein, thereby producing the fusion protein.

13. A pharmaceutical composition comprising the fusion protein of claim 1.

14. A method of treatment of inflammatory and interstitial lung diseases, comprising administering the fusion protein of claim 1 to a mammal at a dose sufficient to treat the disease.

15. The method according to claim 14, wherein the fusion protein is administered to a mammal by an administration selected from the group consisting of parenteral administration, non-parenteral (enteral) administration, and topical administration.

16. The method according to claim 15, wherein parenteral administration is by aerosol administration or intratracheal instillation.

17. A fusion protein comprising:
   (a) a mature mammalian surfactant protein, and
   (b) a mammalian plasminogen activator,
   wherein the mature surfactant protein is fused at its C-terminus or its N-terminus to the N-terminus or the C-terminus of the plasminogen activator, respectively, wherein the surfactant protein is selected from the group consisting of surfactant protein B (SP-B) and surfactant protein C (SP-C), and wherein the fusion protein retains the biological activities of the surfactant protein and the plasminogen activator.

18. The fusion protein of claim 17, wherein one of the protein components (a) or (b) is a human protein.

19. The fusion protein of claim 17, wherein both protein components (a) and (b) are human proteins.

20. The fusion protein of claim 17, wherein the mature surfactant protein is surfactant protein B (SP-B).

21. The fusion protein according to claim 17 comprising the mature surfactant protein B (SP-B) fused to the low molecular weight two-chain u-PA (LMW-u-PA), as shown in SEQ ID NO: 25 and SEQ ED NO: 26, respectively.

22. The fusion protein of claim 17, wherein the mammalian plasminogen activator is selected from the group consisting of high molecular weight two-chain urokinase-plasminogen activator (HMW-u-PA), low molecular weight two-chain u-PA (LMW-u-PA), low molecular weight u-PA B-chain, recombinant single-chain u-PA (r-scu-PA), tissue plasminogen activator (t-PA), recombinant t-PA (rt-PA), its variants r-PA, n-PA, and TNK-t-PA, and catalytically active mutants of the plasminogen activator.

23. A nucleic acid molecule comprising a nucleotide sequence encoding the fusion protein of claim 17.

24. A method for production of the fusion protein of claim 17, comprising:
introducing a nucleic acid molecule encoding the fusion protein into a suitable vector, and
introducing the recombinant vector into a suitable host cell or into a suitable cell extract under conditions suitable for the expression of said nucleic acid molecule encoding the fusion protein, thereby producing the fusion protein.

25. A pharmaceutical composition comprising the fusion protein of claim 17.

26. A method of treatment of inflammatory and interstitial lung diseases, comprising administering the fusion protein of claim 17 to a mammal at a dose sufficient to treat the disease.

27. An isolated nucleic acid molecule comprising the nucleotide sequence of SEQ ID NO: 6 or SEQ ID NO: 7.

28. An isolated nucleic acid molecule comprising the nucleotide sequence of SEQ ID NO: 12 or SEQ ID NO: 13.

* * * * *